US012753417B2

(12) United States Patent
Wang et al.

(10) Patent No.: US 12,753,417 B2
(45) Date of Patent: Oct. 6, 2026

(54) USE OF SARS-CoV-2 RECEPTOR BINDING MOTIF (RBM)-REACTIVE MONOCLONAL ANTIBODIES TO TREAT COVID-19

(71) Applicant: The Feinstein Institutes for Medical Research, Manhasset, NY (US)

(72) Inventors: Haichao Wang, Edison, NJ (US); Kevin J. Tracey, Old Greenwich, CT (US); Jian Hua Li, New York, NY (US); Cassie Zhu, Great Neck, NY (US); Xiaoling Qiang, Hicksville, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 702 days.

(21) Appl. No.: 18/019,548

(22) PCT Filed: Aug. 30, 2021

(86) PCT No.: PCT/US2021/048220
§ 371 (c)(1),
(2) Date: Feb. 3, 2023

(87) PCT Pub. No.: WO2022/051223
PCT Pub. Date: Mar. 10, 2022

(65) Prior Publication Data

US 2023/0287090 A1 Sep. 14, 2023

Related U.S. Application Data

(60) Provisional application No. 63/073,641, filed on Sep. 2, 2020.

(51) Int. Cl.

| | |
|---|---|
| ***C12N 15/86*** | (2006.01) |
| ***A61P 31/14*** | (2006.01) |
| ***C07K 14/005*** | (2006.01) |
| ***C07K 16/104*** | (2026.01) |
| ***C07K 16/108*** | (2026.01) |

(52) U.S. Cl.
CPC .............. *C12N 15/86* (2013.01); *A61P 31/14* (2018.01); *C07K 16/104* (2026.01); *C07K 16/108* (2026.01); *C07K 2317/24* (2013.01); *C07K 2317/92* (2013.01)

(58) Field of Classification Search
CPC ............ C07K 16/1003; C07K 2317/24; C07K 2317/92; C07K 2317/30; C07K 2317/76; C12N 2770/20022
See application file for complete search history.

(56) References Cited

U.S. PATENT DOCUMENTS

2005/0282154 A1* 12/2005 Farzan ............ G01N 33/56983 435/235.1
2008/0248013 A1 10/2008 Ikemoto et al.
2012/0294796 A1 11/2012 Johnson et al.
2015/0018531 A1 1/2015 Saunders et al.
2017/0008961 A1 1/2017 Chi
2018/0346565 A1 12/2018 Arathoon et al.
2020/0190159 A1* 6/2020 Wang .................. A61K 38/178

FOREIGN PATENT DOCUMENTS

WO WO-2021188969 A2 * 9/2021 ............ A61K 39/12
WO WO-2021194423 A1 * 9/2021 ......... C07K 16/1002
WO WO-2021213520 A1 * 10/2021 ......... C07K 16/1003
WO WO-2021239014 A1 * 12/2021 ......... C07K 16/1003

OTHER PUBLICATIONS

Wu et al 2020. A noncompeting pair of human neutralizing antibodies block COVID-19 virus binding to its receptor ACE2. Science, 2020, vol. 368, issue 6496, p. 1274-1278. (Year: 2020).*
Chen, X., Li, R., Pan, Z. et al. Human monoclonal antibodies block the binding of SARS-CoV-2 spike protein to angiotensin converting enzyme 2 receptor. Cell Mol Immunol 17, 647-649 (2020). (Year: 2020).*
Temesgen et al 2020. GM-CSF Neutralization With Lenzilumab in Severe COVID-19 Pneumonia: A Case-Cohort Study. Mayo Clin Proc. Nov. 2020;95(11):2382-2394. (Year: 2020).*
Chi et al 2020. Humanized Single Domain Antibodies Neutralize SARS-CoV-2 by Targeting 3 Spike Receptor Binding Domain. bioRxiv preprint doi: https://doi.org/10.1101/2020.04.14.042010. (Year: 2020).*
Schneider et al 2021.Microfluidic characterisation reveals broad range of SARS-CoV-2 antibody affinity in human plasma. Life Sci Alliance. Nov. 30, 2021;5(2):e202101270. (Year: 2021).*
Dall'Acqua WF, Damschroder MM, Zhang J, Woods RM, Widjaja L, Yu J, Wu H. Antibody humanization by framework shuffling. Methods. May 2005;36(1):43-60. (Year: 2005).*
Nelson B, Sidhu SS. Synthetic antibody libraries. Methods Mol Biol. 2012;899:27-41. (Year: 2012).*
Dong J, Huang B, Jia Z, Wang B, Gallolu Kankanamalage S, Titong A, Liu Y. Development of multi-specific humanized llama antibodies blocking SARS-CoV-2/ACE2 interaction with high affinity and avidity. Emerg Microbes Infect. Dec. 2020;9(1):1034-1036. (Year: 2020).*
Harding FA, Stickler MM, Razo J, DuBridge RB. The immunogenicity of humanized and fully human antibodies: residual immunogenicity resides in the CDR regions. MAbs. May-Jun. 2010;2(3):256-65. (Year: 2010).*
Fransson J, Teplyakov A, Raghunathan G, Chi E, Cordier W, Dinh T, Feng Y, Giles-Komar J, Gilliland G, Lollo B, Malia TJ, Nishioka W, Obmolova G, Zhao S, Zhao Y, Swanson RV, Almagro JC. Human framework adaptation of a mouse anti-human IL-13 antibody. J Mol Biol. Apr. 30, 2010;398(2):214-31. (Year: 2010).*

(Continued)

*Primary Examiner* — Bennett M Celsa
*Assistant Examiner* — Samadhan Jaising Jadhao
(74) *Attorney, Agent, or Firm* — Amster, Rothstein & Ebenstein LLP

(57) ABSTRACT

Provided SARS-CoV-2 receptor binding motif (RBM)-reactive monoclonal antibodies and fragments thereof, which inhibit the interaction between the spike protein RBM and human ACE2, as well as methods of use employing such antibodies and/or fragments.

18 Claims, 23 Drawing Sheets

Specification includes a Sequence Listing.

(56) References Cited

OTHER PUBLICATIONS

Dall'Acqua WF, Kiener PA, Wu H. Properties of human IgG1s engineered for enhanced binding to the neonatal Fc receptor (FcRn). J Biol Chem. Aug. 18, 2006;281(33):23514-24. (Year: 2006).*

Yeung YA, Leabman MK, Marvin JS, Qiu J, Adams CW, Lien S, Starovasnik MA, Lowman HB. Engineering human IgG1 affinity to human neonatal Fc receptor: impact of affinity improvement on pharmacokinetics in primates. J Immunol. Jun. 15, 2009;182(12): 7663-71. (Year: 2009).*

Lee, CH., Kang, T.H., Godon, O. et al. An engineered human Fc domain that behaves like a pH-toggle switch for ultra-long circulation persistence. Nat Commun 10, 5031 (2019). (Year: 2009).*

Florindo, H.F., Kleiner, R., Vaskovich-Koubi, D. et al. Immune-mediated approaches against COVID-19. Nat. Nanotechnol. 15, 630-645 (2020). (Year: 2020).*

Vidarsson G, Dekkers G, Rispens T. IgG subclasses and allotypes: from structure to effector functions. Front Immunol. Oct. 20, 2014;5:520. (Year: 2014).*

Steffen et al 2020. The receptor binding domain of SARS-CoV-2 spike is the key target of neutralizing antibody in human polyclonal sera. bioRxiv preprint doi: https://doi.org/10.1101/2020.08.21.261727; this version posted Aug. 22, 2020. (Year: 2020).*

Tortorici et al 2020. Ultrapotent human antibodies protect against SARS-CoV-2 challenge via multiple mechanisms. Science. Nov. 20, 2020;370(6519):950-957. (Year: 2020).*

Shi et al 2020. A human neutralizing antibody targets the receptor-binding site of SARS-CoV-2. Nature 584, 120-124 (2020). (Year: 2020).*

International Search Report and Written Opinion dated Feb. 2, 2022 issued in PCT International Application No. PCT/US2021/048220.

Wu et al., "A New Coronavirus Associated With Human Respiratory Disease in China," Nature, vol. 579, Mar. 12, 2020, published online Feb. 3, 2020 (retrieved from the internet on Nov. 12, 2021 at <URL:https://www.nature.com/articles/s41586-020-2008-3.pdf>), pp. 265-269.

* cited by examiner

SARS-CoV Spike Protein and Receptor-binding Domain (RBD) and Motif (RBM)

Homology between coronavirus ACE2 RBD and RBM

```
319
RVQPTESIVRFPNITNLCPFGEVFNATRFASVYAWNRKRISNCVADYSVLYNSASFSTFK
||.|:..:|||||||||||||||||||:|:|||||:||:||||||||||||||..|||||
RVVPSGDVVRFPNITNLCPFGEVFNATKFPSVYAWERKKISNCVADYSVLYNSTFFSTFK

                                                           437
CYGVSPTKLNDLCFTNVYADSFVIRGDEVRQIAPGQTGKIADYNYKLPDDFTGCVIAWNS
|||||:||||||||:||||||||::||:|||||||||||||||||||||||.|||:|||:
CYGVSATKLNDLCFSNVYADSFVVKGDDVRQIAPGQTGVIADYNYKLPDDFMGCVLAWNT
          @   @ @@                  @          @@ @   @  @ @
NNLDSKVGGNYNYLYRLFRKSNLKPFERDISTEIYQAGSTPCNGVEGFNCYFPLQSYGFQ
.|:|....|||||.||..|:..|:||||||||..:::...|| .:.:.|||:||:.|||:
RNIDATSTGNYNYKYRYLRHGKLRPFERDISNVPFSPDGKPC-TPPALNCYWPLNDYGFY
 @@@  @  508                              541
PTNGVGYQPYRVVVLSFELLHAPATVCGPKKSTNLVKNKCVNF      (SARS-CoV-2)
.|.|:|||||||||||||||:|||||||||.||:|:||:||||
TTTGIGYQPYRVVVLSFELLNAPATVCGPKLSTDLIKNQCVNF      (SARS-CoV)
```

Fig. 1(B)

Homology between RBM sequence of wildtype and mutant SARS-CoV-2

```
437                                            484                     508
NSNNLDSKVGGNYNYLYRLFRKSNLKPFERDISTEIYQAGSTPCNGVEGFNCYFPLQSYGFQPTNGVGYQPY   (RBM wild-type)
            @   @ @@                  @          @@ @   @  @ @ @@@  @      (ACE2 binding)
NSNNLDSKVGGNYNYLYRLFRKSNLKPFERDISTEIYQAGSTPCNGVKGFNCYFPLQSYGFQPTNGVGYQPY   (RBM-m mutant)
                                               ↑
```

Fig. 1(D)

Homology between SARS-CoV-2 RBM and human or murine TN

```
449 YNYLYR 454    (SASR-CoV-2)
    |:|| |
NDALYEYL-RQ       (human TN)
|:||:||: |:
NEALFEYA-RH       (murine TN)
```

Fig. 1(E)

*SEQ ID NO 1*

Human tetranectin amino acid sequence:

```
1         10        20        30        40        50        60        70
MELWGAYLLICLFSLLTQVTTEPPTQKPKKIVNAKKDVVNTKMFEELKSRLDTLAQEVALLKEQQALQTV

71        80        90        100       110       120       130       140
CLKGTKVHMKCFLAFTQTKTFHEASEDCISRGGTLSTPQTGSENDALYEYLRQSVGNEAEIWLGLNDMAA

141       150       160       170       180       190       200
EGTWVDMTGARIAYKNWETEITAQPDGGKTENCAVLSGAANGKWFDKRCRDQLPYICQFGIV
```

(residues 113–122, NDALYEYLRQ, printed bold and underlined)

Fig. 7

SEQ ID NO 2

Epitope sequence

NDALYEYLRQ

Fig. 8

The receptor binding domain (RBD) and receptor-binding motif (RBM) of SARS-CoV and SARS-CoV-2

```
319
RVQPTESIVRFPNITNLCPFGEVFNATRFASVYAWNRKRISNCVADYSVLYNSASFSTFK
||.|:..:|||||||||||||||||||:|:|||||:||:||||||||||||||..|||||
RVVPSGDVVRFPNITNLCPFGEVFNATKFPSVYAWERKKISNCVADYSVLYNSTFFSTFK

                                                         437
CYGVSPTKLNDLCFTNVYADSFVIRGDEVRQIAPGQTGKIADYNYKLPDDFTGCVIAWNS
|||||:||||||||:||||||||::||:||||||||||.||||||||||||.|||:|||:
CYGVSATKLNDLCFSNVYADSFVVKGDDVRQIAPGQTGVIADYNYKLPDDFMGCVLAWNT
          @   @ @@                  @          @@ @   @  @ @
NNLDSKVGGNYNYLYRLFRKSNLKPFERDISTEIYQAGSTPCNGVEGFNCYFPLQSYGFQ
.|:|....|||||.||..|:..|:|||||||..:.:....||  .:.:.|||:||:.|||:
RNIDATSTGNYNYKYRYLRHGKLRPFERDISNVPFSPDGKPC-TPPALNCYWPLNDYGFY

 @@@  @  508                              541
PTNGVGYQPYRVVVLSFELLHAPATVCGPKKSTNLVKNKCVNF        (SARS-CoV-2)
.|.|:||||||||||||||:|||||||||.||:|:||:||||
TTTGIGYQPYRVVVLSFELLNAPATVCGPKLSTDLIKNQCVNF        (SARS-CoV)
```

Fig. 9

Homology between a sequence in the RBM of SARS-CoV-2 and the epitope sequence of all claimed mAbs

```
449 YNYLYR 454     (SASR-CoV-2)
    |:||  |
NDALYEYL-RQ        (human TN)
```

Fig. 10

| CDR1-H | CDR2-H | CDR3-H | Clone # | KD TN | KD RBM |
|---|---|---|---|---|---|
| TDYMS | AINSNGGTTYYPDTVKG | QVKNGLDY | 27B12 (**mAb8**) | 2.02e-9 | 1.74e-8 |
| SYYMS | AINSNGGRTYYPDTVKG | QGKNGLDY | 25B2 (**mAb6**) | 9.15e-10 | 1.80e-7 |
| SSYMS | AINNNGGTTYYPDTVKG | QGKNGLDY | 23F6 (**mAb5**) | 8.03e-9 | **ND** |
| SDYMS | AINSNGGTTYYPDTVKG | QGKNGMDY | 18B1 (**mAb2**) | 1.14e-10 | 6.28e-8 |

| CDR1-L | CDR2-L | CDR3-L | Clone # | KD TN | KD RBM |
|---|---|---|---|---|---|
| RASQDISNYLN | KTSRLHS | QQGNTLPPT | 27B12 (**mAb8**) | 2.02e-9 | 1.74e-8 |
| RASQDISNHLN | YTSRLHS | QQGKTLPPT | 25B2 (**mAb6**) | 9.15e-10 | 1.80e-7 |
| RASQDIGNLLN | YTSRLHS | QQANTLPPT | 23F6 (**mAb5**) | 8.03e-9 | **ND** |
| RASQDISNHLN | YTSRLHS | QQGKTLPPT | 18B1 (**mAb2**) | 1.14e-10 | 6.28e-8 |

Fig. 11

| *Signal* | FR1 | CDR1 | FR2 | CDR2 | FR3 | CDR3 | FR4 | |
|---|---|---|---|---|---|---|---|---|
| *MNFGLRLIFLVLVLKGVLC* | DVNLVESGGGLVKLGGSLKLSCADSGFTFS | **SYYMS** | WVRQTPEKRLELVA | **AINSNGGRTYYPDTVKG** | RFTISRDNAKNTLYLQMSSLKSEDTALYYCAR | **QGKNGLDY** | WGQGTSVTVSS | m |
| *MNFGLRLIFLVLVLKGVLC* | DVKLVESGGGLVKLGGSLKLSCAASGFTFS | **TDYMS** | WVRQSPEKRLELVA | **AINSNGGTTYYPDTVKG** | RFTISRDNAKNTLYLQMSSLRSEDTALYYCAR | **QVKNGLDY** | WGQGTSVTVSS | m |
| *MNFGLRLIFLVLVLKGVLC* | DVKLVESGGGLVKLGGSLKLSCAASGFTFS | **SSYMS** | WVRQTPEKRLELVA | **AINNNGGTTYYPDTVKG** | RFTISRDNAKNTLYLQMSSLKSEDTALYYCTR | **QGKNGLDY** | WGQGTSVTVSS | m |
| *MNFGLRLIFLVLVLKGVLC* | DVKLVESGGGLVNLGGSLKLSCAASGFTFS | **SDYMS** | WVRQIPEKRLELVA | **AINSNGGTTYYPDTVKG** | RFTISRDNAKNTLYLQMSSLKSEDTALYYCAR | **QGKNGMDY** | WGQGTSVTVSS | m |

| *Signal* | FR1 | CDR1 | FR2 | CDR2 | FR3 | CDR3 | FR4 | |
|---|---|---|---|---|---|---|---|---|
| *MSSAQFLGLLLLCFQGTRC* | DIQMTQTTSSLSASLGDRVTISC | **RASQDISNHLN** | WYQQKPDGTIKLLIY | **YTSRLHS** | GVPSRFSGSGSGTDFSLSISNLEQEDIATYFC | **QQGKTLPPT** | FGGGTKLEIK | **mAb8 (L)** |
| *MMSSAQFLSLLLLCFQGTRC* | DIQMTQTTSSLSASLGDRVTISC | **RASQDISNYLN** | WYQQKPDGTVKLLIY | **KTSRLHS** | GVPSRFRGSGSGTDYSLTISNLEEEDVATYFC | **QQGNTLPPT** | FGGGTKLEIK | **mAb6 (L)** |
| *MSSAQFLGLLLLCFQGTRC* | DIQMTQTTSSLSASLGDRVTISC | **RASQDIGNLLN** | WYQQKPDGTVKLLIS | **YTSRLHS** | GVPSRFSGSGSGTDYSLTITNLEQEDIATYFC | **QQANTLPPT** | FGGGSKLEIK | **mAb5 (L)** |
| *MSSAQFLGLLLLCFQGTRC* | DIQMTQTTSSLSASLGDRVTISC | **RASQDISNHLN** | WYQQRPDGTVKLLIY | **YTSRLHS** | GVPSRFSGSGSGTDYSFTITNLDQEDIATYFC | **QQGKTLPPT** | FGGGTKLEIK | **mAb2 (L)** |

Fig. 12

SEQUENCE LISTING

```
<160> NUMBER OF SEQ ID NOS: 47

<210> SEQ ID NO 1
<211> LENGTH: 202
<212> TYPE: PRT
<213> ORGANISM: HOMO SAPIENS

<400> SEQUENCE: 1

Met Glu Leu Trp Gly Ala Tyr Leu Leu Leu Cys Leu Phe Ser Leu Leu
1               5                   10                  15

Thr Gln Val Thr Thr Glu Pro Pro Thr Gln Lys Pro Lys Lys Ile Val
            20                  25                  30

Asn Ala Lys Lys Asp Val Val Asn Thr Lys Met Phe Glu Glu Leu Lys
        35                  40                  45

Ser Arg Leu Asp Thr Leu Ala Gln Glu Val Ala Leu Leu Lys Glu Gln
    50                  55                  60

Gln Ala Leu Gln Thr Val Cys Leu Lys Gly Thr Lys Val His Met Lys
65                  70                  75                  80

Cys Phe Leu Ala Phe Thr Gln Thr Lys Thr Phe His Glu Ala Ser Glu
                85                  90                  95

Asp Cys Ile Ser Arg Gly Gly Thr Leu Ser Thr Pro Gln Thr Gly Ser
            100                 105                 110

Glu Asn Asp Ala Leu Tyr Glu Tyr Leu Arg Gln Ser Val Gly Asn Glu
        115                 120                 125

Ala Glu Ile Trp Leu Gly Leu Asn Asp Met Ala Ala Glu Gly Thr Trp
    130                 135                 140
```

Val Asp Met Thr Gly Ala Arg Ile Ala Tyr Lys Asn Trp Glu Thr Glu
145 150 155 160

Ile Thr Ala Gln Pro Asp Gly Gly Lys Thr Glu Asn Cys Ala Val Leu
165 170 175

Ser Gly Ala Ala Asn Gly Lys Trp Phe Asp Lys Arg Cys Arg Asp Gln
180 185 190

Leu Pro Tyr Ile Cys Gln Phe Gly Ile Val
195 200

<210> SEQ ID NO 2
<211> LENGTH: 10
<212> TYPE: PRT
<213> ORGANISM: HOMO SAPIENS

<400> SEQUENCE: 2

Asn Asp Ala Leu Tyr Glu Tyr Leu Arg Gln
1 5 10

<210> SEQ ID NO 3
<211> LENGTH: 72
<212> TYPE: PRT
<213> ORGANISM: SARS COV-2

<400> SEQUENCE: 3

Asn Ser Asn Asn Leu Asp Ser Lys Val Gly Gly Asn Tyr Asn Tyr Leu
1 5 10 15

Tyr Arg Leu Phe Arg Lys Ser Asn Leu Lys Pro Phe Glu Arg Asp Ile
20 25 30

Ser Thr Glu Ile Tyr Gln Ala Gly Ser Thr Pro Cys Asn Gly Val Glu
35 40 45

Gly Phe Asn Cys Tyr Phe Pro Leu Gln Ser Tyr Gly Phe Gln Pro Thr
50 55 60

Asn Gly Val Gly Tyr Gln Pro Tyr
65 70

<210> SEQ ID NO 4
<211> LENGTH: 6
<212> TYPE: PRT
<213> ORGANISM: SARS COV-2

<400> SEQUENCE: 4

Tyr Asn Tyr Leu Tyr Arg
1 5

<210> SEQ ID NO 5
<211> LENGTH: 408
<212> TYPE: DNA
<213> ORGANISM: MURINE SP.

<400> SEQUENCE: 5
atgaacttcg ggctcagatt gattttcctt gtccttgttt taaaaggtgt cctgtgtgac 60
gtgaagctcg tggagtctgg gggaggctta gtgaagcttg gagggtccct gaaactctcc 120
tgtgcagcct ctggattcac tttcagtacc gattacatgt cttgggttcg ccagagtcca 180
gagaagaggc tggagttggt cgcagccatt aatagtaatg gtggtaccac ctactatcca 240
gacactgtga agggccgatt catcatctcc agagacaatg ccaagaacac cctgtacctg 300
caaatgagca gtctgaggtc tgaggacaca gccttgtatt actgtgcaag acaggttaag 360
aatggtctgg actactgggg tcaaggaacc tcagtcaccg tctcctca 408

<210> SEQ ID NO 6
<211> LENGTH: 136
<212> TYPE: PRT
<213> ORGANISM: MURINE SP.

<400> SEQUENCE: 6

```
Met Asn Phe Gly Leu Arg Leu Ile Phe Leu Val Leu Val Leu Lys Gly
1               5                   10                  15

Val Leu Cys Asp Val Lys Leu Val Glu Ser Gly Gly Gly Leu Val Lys
            20                  25                  30

Leu Gly Gly Ser Leu Lys Leu Ser Cys Ala Ala Ser Gly Phe Thr Phe
        35                  40                  45

Ser Thr Asp Tyr Met Ser Trp Val Arg Gln Ser Pro Glu Lys Arg Leu
    50                  55                  60

Glu Leu Val Ala Ala Ile Asn Ser Asn Gly Gly Thr Thr Tyr Tyr Pro
65                  70                  75                  80

Asp Thr Val Lys Gly Arg Phe Ile Ile Ser Arg Asp Asn Ala Lys Asn
                85                  90                  95

Thr Leu Tyr Leu Gln Met Ser Ser Leu Arg Ser Glu Asp Thr Ala Leu
            100                 105                 110

Tyr Tyr Cys Ala Arg Gln Val Lys Asn Gly Leu Asp Tyr Trp Gly Gln
        115                 120                 125

Gly Thr Ser Val Thr Val Ser Ser
    130                 135
```

<210> SEQ ID NO 7
<211> LENGTH: 381
<212> TYPE: DNA
<213> ORGANISM: MURINE SP.

<400> SEQUENCE: 7

```
atgatgtcct ctgctcagtt ccttggtctc ctgttgctct gttttcaagg taccagatgt      60

gatatccaga tgacacagac tacatcctcc ctgtctgcct ctctgggaga cagagtcacc     120

atcagttgca gggcaagtca ggacattagc aattatttaa actggtatca gcagaaacca     180

gatggaactg tcaaactcct gatctacaaa acttctagat tacactcagg agtcccatca     240

aggttcagag gcagtgggtc tggaacagat tattctctca ccattagcaa cctggaggaa     300

gaagatgttg ccacttactt ttgccaacag ggtaatacgc ttcctccgac gttcggtgga     360

ggcaccaagc tggaaatcaa a                                               381
```

<210> SEQ ID NO 8
<211> LENGTH: 127
<212> TYPE: PRT
<213> ORGANISM: MURINE SP.

<400> SEQUENCE: 8

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Lys Thr Ser Arg Leu His Ser Gly Val Pro Ser
```

```
65                  70                  75                  80

Arg Phe Arg Gly Ser Gly Ser Gly Thr Asp Tyr Ser Leu Thr Ile Ser
                85                  90                  95

Asn Leu Glu Glu Glu Asp Val Ala Thr Tyr Phe Cys Gln Gln Gly Asn
            100                 105                 110

Thr Leu Pro Pro Thr Phe Gly Gly Gly Thr Lys Leu Glu Ile Lys
        115                 120                 125


<210> SEQ ID NO 9
<211> LENGTH: 408
<212> TYPE: DNA
<213> ORGANISM: MURINE SP.

<400> SEQUENCE: 9

atgaacttcg ggctcagatt gattttcctt gtccttgttt taaaaggtgt cctgtgtgac      60

gtgaacctcg tggagtcggg gggaggctta gtgaagcttg gagggtccct gaaactctcc     120

tgtgcagact ctggattcac tttcagtagc tattacatgt cttgggttcg ccagactcca     180

gagaagaggc tggagttggt cgcagccatt aatagtaatg gtggtaggac ctactatcca     240

gacactgtga agggccgatt caccatctcc agagacaatg ccaagaacac cctgtacctg     300

caaatgagca gtctgaagtc tgaggacaca gccttgtatt actgtgcaag acagggtaag     360

aatggtttgg actactgggg tcaaggaacc tcagtcaccg tctcctca                  408


<210> SEQ ID NO 10
<211> LENGTH: 136
<212> TYPE: PRT
<213> ORGANISM: MURINE SP.

<400> SEQUENCE: 10

Met Asn Phe Gly Leu Arg Leu Ile Phe Leu Val Leu Val Leu Lys Gly
1               5                   10                  15

Val Leu Cys Asp Val Asn Leu Val Glu Ser Gly Gly Gly Leu Val Lys
            20                  25                  30

Leu Gly Gly Ser Leu Lys Leu Ser Cys Ala Asp Ser Gly Phe Thr Phe
        35                  40                  45

Ser Ser Tyr Tyr Met Ser Trp Val Arg Gln Thr Pro Glu Lys Arg Leu
    50                  55                  60

Glu Leu Val Ala Ala Ile Asn Ser Asn Gly Gly Arg Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Leu
            100                 105                 110

Tyr Tyr Cys Ala Arg Gln Gly Lys Asn Gly Leu Asp Tyr Trp Gly Gln
        115                 120                 125

Gly Thr Ser Val Thr Val Ser Ser
    130                 135


<210> SEQ ID NO 11
<211> LENGTH: 378
<212> TYPE: DNA
<213> ORGANISM: MURINE SP.

<400> SEQUENCE: 11

atgtcctctg ctcagttcct tggtctcctg ttgctctgtt ttcaaggtac cagatgtgat      60

atccagatga cacagaccac atcctccctg tctgcctctc tgggagacag agtcaccatc     120
```

-continued

```
agttgcaggg caagtcagga cattagtaat catttaaact ggtatcagca gaaaccagat    180

ggaactatta aactcctgat ctactataca tcaagattac actcaggagt cccatcaagg    240

ttcagtggca gtgggtctgg aactgatttt tctctcagca ttagcaacct ggagcaagag    300

gatattgcca cttacttttg ccaacagggt aaaacgcttc ctccgacgtt cggtggaggc    360

accaaactgg aaatcaaa                                                  378


<210> SEQ ID NO 12
<211> LENGTH: 126
<212> TYPE: PRT
<213> ORGANISM: MURINE SP.

<400> SEQUENCE: 12

Met Ser Ser Ala Gln Phe Leu Gly Leu Leu Leu Leu Cys Phe Gln Gly
1               5                   10                  15

Thr Arg Cys Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Asn His Leu Asn Trp Tyr Gln Gln Lys Pro Asp Gly Thr Ile Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Ser Leu Ser Ile Ser Asn
                85                  90                  95

Leu Glu Gln Glu Asp Ile Ala Thr Tyr Phe Cys Gln Gln Gly Lys Thr
            100                 105                 110

Leu Pro Pro Thr Phe Gly Gly Gly Thr Lys Leu Glu Ile Lys
        115                 120                 125


<210> SEQ ID NO 13
<211> LENGTH: 408
<212> TYPE: DNA
<213> ORGANISM: MURINE SP.

<400> SEQUENCE: 13

atgaacttcg ggctcagatt gattttcctt gtccttgttt taaaaggtgt cctgtgtgac     60

gtgaagctcg tggagtctgg gggtggctta gtgaaacttg gagggtccct gaaactctcc    120

tgtgcagcct ctggattcac tttcagtagc tcttacatgt cttgggttcg ccagactcca    180

gagaagaggc tggagttggt cgcagccatt aataataatg gtggtaccac ctactatcca    240

gacactgtga agggccgatt cactatctcc agagacaatg ccaagaacac cctgtacctg    300

caaatgagca gtctgaagtc tgaggacaca gccttgtatt attgtacaag acagggtaag    360

aatggtttgg actactgggg tcaaggaacc tcagtcaccg tctcctca                 408


<210> SEQ ID NO 14
<211> LENGTH: 136
<212> TYPE: PRT
<213> ORGANISM: MURINE SP.

<400> SEQUENCE: 14

Met Asn Phe Gly Leu Arg Leu Ile Phe Leu Val Leu Val Leu Lys Gly
1               5                   10                  15

Val Leu Cys Asp Val Lys Leu Val Glu Ser Gly Gly Gly Leu Val Lys
            20                  25                  30
```

-continued

```
Leu Gly Gly Ser Leu Lys Leu Ser Cys Ala Ala Ser Gly Phe Thr Phe
        35                  40                  45

Ser Ser Ser Tyr Met Ser Trp Val Arg Gln Thr Pro Glu Lys Arg Leu
    50                  55                  60

Glu Leu Val Ala Ala Ile Asn Asn Asn Gly Gly Thr Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Leu
            100                 105                 110

Tyr Tyr Cys Thr Arg Gln Gly Lys Asn Gly Leu Asp Tyr Trp Gly Gln
        115                 120                 125

Gly Thr Ser Val Thr Val Ser Ser
    130                 135


<210> SEQ ID NO 15
<211> LENGTH: 378
<212> TYPE: DNA
<213> ORGANISM: MURINE SP.

<400> SEQUENCE: 15

atgtcctctg ctcagttcct tggtctcctg ttgctctgtt ttcaaggtac cagatgtgat      60

atccagatga cacagactac atcctccctg tctgcctctc tgggagacag agtcaccatc     120

agttgcaggg ccagtcagga cattggcaat cttttaaact ggtatcagca gaaaccagat     180

ggaactgtta aactcctgat ctcctacaca tcaagattac actcaggagt cccatcaagg     240

ttcagtggca gtgggtctgg aacagattat tctctcacca ttaccaacct ggaacaagaa     300

gatattgcca cttacttttg ccaacaggct aatacgcttc ctccgacgtt cggtggaggc     360

tccaagctgg aaatcaaa                                                   378


<210> SEQ ID NO 16
<211> LENGTH: 126
<212> TYPE: PRT
<213> ORGANISM: MURINE SP.

<400> SEQUENCE: 16

Met Ser Ser Ala Gln Phe Leu Gly Leu Leu Leu Leu Cys Phe Gln Gly
1               5                   10                  15

Thr Arg Cys Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Gly Asn Leu Leu Asn Trp Tyr Gln Gln Lys Pro Asp Gly Thr Val Lys
    50                  55                  60

Leu Leu Ile Ser Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Thr Asn
                85                  90                  95

Leu Glu Gln Glu Asp Ile Ala Thr Tyr Phe Cys Gln Gln Ala Asn Thr
            100                 105                 110

Leu Pro Pro Thr Phe Gly Gly Gly Ser Lys Leu Glu Ile Lys
        115                 120                 125


<210> SEQ ID NO 17
<211> LENGTH: 408
<212> TYPE: DNA
```

<213> ORGANISM: MURINE SP.

<400> SEQUENCE: 17

```
atgaacttcg ggctcagatt gattttcctt gtccttgttt taaaaggtgt cctgtgtgac     60

gtgaagctcg tggagtctgg gggaggctta gtgaaccttg gagggtccct gaaactctcc    120

tgtgcagcct ctggattcac tttcagtagc gattacatgt cttgggttcg ccagattcca    180

gagaagaggc tggagttggt cgcagccatt aatagtaatg gtggtaccac ctactatcca    240

gacactgtga agggccgatt caccatctcc agagacaatg ccaagaacac cctgtacctg    300

caaatgagca gtctgaagtc tgaggacaca gccttgtatt actgtgcaag acagggtaag    360

aatggtatgg actactgggg tcaaggaacc tcagtcaccg tctcctca                408
```

<210> SEQ ID NO 18
<211> LENGTH: 136
<212> TYPE: PRT
<213> ORGANISM: MURINE SP.

<400> SEQUENCE: 18

```
Met Asn Phe Gly Leu Arg Leu Ile Phe Leu Val Leu Val Leu Lys Gly
1               5                   10                  15

Val Leu Cys Asp Val Lys Leu Val Glu Ser Gly Gly Gly Leu Val Asn
            20                  25                  30

Leu Gly Gly Ser Leu Lys Leu Ser Cys Ala Ala Ser Gly Phe Thr Phe
        35                  40                  45

Ser Ser Asp Tyr Met Ser Trp Val Arg Gln Ile Pro Glu Lys Arg Leu
    50                  55                  60

Glu Leu Val Ala Ala Ile Asn Ser Asn Gly Gly Thr Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Leu
            100                 105                 110

Tyr Tyr Cys Ala Arg Gln Gly Lys Asn Gly Met Asp Tyr Trp Gly Gln
        115                 120                 125

Gly Thr Ser Val Thr Val Ser Ser
    130                 135
```

<210> SEQ ID NO 19
<211> LENGTH: 378
<212> TYPE: DNA
<213> ORGANISM: MURINE SP.

<400> SEQUENCE: 19

```
atgtcctctg ctcagttcct tggtctcctg ttgctctgtt ttcaaggtac cagatgtgat     60

atccagatga cacagactac atcctccctg tctgcctctc tgggagacag agtcaccatc    120

agttgcaggg caagtcagga cattagcaat catttaaact ggtatcagca gagaccagat    180

ggaactgtta aactcctgat ctactacaca tcaagattac actcaggagt cccatcaagg    240

ttcagtggca gtgggtctgg aacagattat tctttcacca ttaccaacct tgatcaagaa    300

gatattgcca cttacttttg ccaacagggt aagacgcttc ctccgacgtt cggtggaggc    360

accaagctgg aaatcaaa                                                  378
```

<210> SEQ ID NO 20
<211> LENGTH: 126
<212> TYPE: PRT

<213> ORGANISM: MURINE SP.

<400> SEQUENCE: 20

Met Ser Ser Ala Gln Phe Leu Gly Leu Leu Leu Leu Cys Phe Gln Gly
1               5                   10                  15

Thr Arg Cys Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Ser Asn His Leu Asn Trp Tyr Gln Gln Arg Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Phe Thr Ile Thr Asn
                85                  90                  95

Leu Asp Gln Glu Asp Ile Ala Thr Tyr Phe Cys Gln Gln Gly Lys Thr
            100                 105                 110

Leu Pro Pro Thr Phe Gly Gly Gly Thr Lys Leu Glu Ile Lys
        115                 120                 125

<210> SEQ ID NO 21
<211> LENGTH: 5
<212> TYPE: PRT
<213> ORGANISM: MURINE SP.

<400> SEQUENCE: 21

Thr Asp Tyr Met Ser
1               5

<210> SEQ ID NO 22
<211> LENGTH: 17
<212> TYPE: PRT
<213> ORGANISM: MURINE SP.

<400> SEQUENCE: 22

Ala Ile Asn Ser Asn Gly Gly Thr Thr Tyr Tyr Pro Asp Thr Val Lys
1               5                   10                  15

Gly

<210> SEQ ID NO 23
<211> LENGTH: 8
<212> TYPE: PRT
<213> ORGANISM: MURINE SP.

<400> SEQUENCE: 23

Gln Val Lys Asn Gly Leu Asp Tyr
1               5

<210> SEQ ID NO 24
<211> LENGTH: 11
<212> TYPE: PRT
<213> ORGANISM: MURINE SP.

<400> SEQUENCE: 24

Arg Ala Ser Gln Asp Ile Ser Asn Tyr Leu Asn
1               5                   10

<210> SEQ ID NO 25
<211> LENGTH: 7
<212> TYPE: PRT
<213> ORGANISM: MURINE SP.

<400> SEQUENCE: 25

Lys Thr Ser Arg Leu His Ser
1 5

<210> SEQ ID NO 26
<211> LENGTH: 9
<212> TYPE: PRT
<213> ORGANISM: MURINE SP.

<400> SEQUENCE: 26

Gln Gln Gly Asn Thr Leu Pro Pro Thr
1 5

<210> SEQ ID NO 27
<211> LENGTH: 5
<212> TYPE: PRT
<213> ORGANISM: MURINE SP.

<400> SEQUENCE: 27

Ser Tyr Tyr Met Ser
1 5

<210> SEQ ID NO 28
<211> LENGTH: 17
<212> TYPE: PRT
<213> ORGANISM: MURINE SP.

<400> SEQUENCE: 28

Ala Ile Asn Ser Asn Gly Gly Arg Thr Tyr Tyr Pro Asp Thr Val Lys
1 5 10 15

Gly

<210> SEQ ID NO 29
<211> LENGTH: 8
<212> TYPE: PRT
<213> ORGANISM: MURINE SP.

<400> SEQUENCE: 29

Gln Gly Lys Asn Gly Leu Asp Tyr
1 5

<210> SEQ ID NO 30
<211> LENGTH: 11
<212> TYPE: PRT
<213> ORGANISM: MURINE SP.

<400> SEQUENCE: 30

Arg Ala Ser Gln Asp Ile Ser Asn His Leu Asn
1 5 10

<210> SEQ ID NO 31
<211> LENGTH: 7
<212> TYPE: PRT
<213> ORGANISM: MURINE SP.

<400> SEQUENCE: 31

Tyr Thr Ser Arg Leu His Ser
1 5

<210> SEQ ID NO 32
<211> LENGTH: 9
<212> TYPE: PRT
<213> ORGANISM: MURINE SP.

<400> SEQUENCE: 32

Gln Gln Gly Lys Thr Leu Pro Pro Thr
1 5

<210> SEQ ID NO 33
<211> LENGTH: 5
<212> TYPE: PRT
<213> ORGANISM: MURINE SP.

<400> SEQUENCE: 33

Ser Ser Tyr Met Ser
1 5

<210> SEQ ID NO 34
<211> LENGTH: 17
<212> TYPE: PRT
<213> ORGANISM: MURINE SP.

<400> SEQUENCE: 34

Ala Ile Asn Asn Asn Gly Gly Thr Thr Tyr Tyr Pro Asp Thr Val Lys
1 5 10 15

Gly

<210> SEQ ID NO 35
<211> LENGTH: 8
<212> TYPE: PRT
<213> ORGANISM: MURINE SP.

<400> SEQUENCE: 35

Gln Gly Lys Asn Gly Leu Asp Tyr
1 5

<210> SEQ ID NO 36
<211> LENGTH: 11
<212> TYPE: PRT
<213> ORGANISM: MURINE SP.

<400> SEQUENCE: 36

Arg Ala Ser Gln Asp Ile Gly Asn Leu Leu Asn
1 5 10

<210> SEQ ID NO 37
<211> LENGTH: 7
<212> TYPE: PRT
<213> ORGANISM: MURINE SP.

<400> SEQUENCE: 37

Tyr Thr Ser Arg Leu His Ser
1 5

<210> SEQ ID NO 38
<211> LENGTH: 9
<212> TYPE: PRT
<213> ORGANISM: MURINE SP.

<400> SEQUENCE: 38

Gln Gln Ala Asn Thr Leu Pro Pro Thr
1 5

<210> SEQ ID NO 39
<211> LENGTH: 5
<212> TYPE: PRT
<213> ORGANISM: MURINE SP.

<400> SEQUENCE: 39

Ser Asp Tyr Met Ser
1 5

<210> SEQ ID NO 40
<211> LENGTH: 17
<212> TYPE: PRT
<213> ORGANISM: MURINE SP.

<400> SEQUENCE: 40

Ala Ile Asn Ser Asn Gly Gly Thr Thr Tyr Tyr Pro Asp Thr Val Lys
1 5 10 15

Gly

<210> SEQ ID NO 41
<211> LENGTH: 8
<212> TYPE: PRT
<213> ORGANISM: MURINE SP.

<400> SEQUENCE: 41

Gln Gly Lys Asn Gly Met Asp Tyr
1 5

<210> SEQ ID NO 42
<211> LENGTH: 11
<212> TYPE: PRT
<213> ORGANISM: MURINE SP.

<400> SEQUENCE: 42

Arg Ala Ser Gln Asp Ile Ser Asn His Leu Asn
1 5 10

<210> SEQ ID NO 43
<211> LENGTH: 7
<212> TYPE: PRT
<213> ORGANISM: MURINE SP.

<400> SEQUENCE: 43

Tyr Thr Ser Arg Leu His Ser
1 5

<210> SEQ ID NO 44
<211> LENGTH: 9
<212> TYPE: PRT
<213> ORGANISM: MURINE SP.

<400> SEQUENCE: 44

Gln Gln Gly Lys Thr Leu Pro Pro Thr
1 5

<210> SEQ ID NO 45
<211> LENGTH: 71
<212> TYPE: PRT
<213> ORGANISM: SARS COV

<400> SEQUENCE: 45

Asn Thr Arg Asn Ile Asp Ala Thr Ser Thr Gly Asn Tyr Asn Tyr Lys
1 5 10 15

Tyr Arg Tyr Leu Arg His Gly Lys Leu Arg Pro Phe Glu Arg Asp Ile
20 25 30

Ser Asn Val Pro Phe Ser Pro Asp Gly Lys Pro Cys Thr Pro Pro Ala
35 40 45

```
Leu Asn Cys Tyr Trp Pro Leu Asn Asp Tyr Gly Phe Tyr Thr Thr Thr
    50                  55                  60

Gly Ile Gly Tyr Gln Pro Tyr
65                  70


<210> SEQ ID NO 46
<211> LENGTH: 222
<212> TYPE: PRT
<213> ORGANISM: SARS COV

<400> SEQUENCE: 46

Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80

Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Tyr Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220


<210> SEQ ID NO 47
<211> LENGTH: 223
<212> TYPE: PRT
<213> ORGANISM: SARS COV2

<400> SEQUENCE: 47

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80
```

-continued

```
Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

USE OF SARS-CoV-2 RECEPTOR BINDING MOTIF (RBM)-REACTIVE MONOCLONAL ANTIBODIES TO TREAT COVID-19

CROSS-REFERENCE TO RELATED APPLICATIONS

This application is a U.S. national stage entry under 35 U.S.C. § 371 of PCT International Patent Application No. PCT/US2021/048220, filed Aug. 30, 2021, which claims benefit of U.S. Provisional Application No. 63/073,641, filed Sep. 2, 2020, the contents of which are hereby incorporated by reference.

STATEMENT OF GOVERNMENT SUPPORT

This invention was made with government support under grant numbers GM063075 and AT005076 awarded by the National Institutes of Health. The government has certain rights in the invention.

BACKGROUND OF THE INVENTION

Shortly after the 2003 outbreak of the severe acute respiratory syndrome (SARS) caused by a β-coronavirus (SARS-CoV) [1], the SARS-like coronavirus 2, SARS-CoV-2 emerged and spread rapidly, causing pandemic COVID-19 that is catastrophically damaging to global human health. As of 28 Aug. 2020, more than 24 million people have been infected, leading to more than 827,000 deaths in 216 countries (who.int/emergencies/diseases/novel-coronavirus-2019). Like the SARS-CoV [1], SARS-CoV-2 viruses also employ envelope spike (S) glycoproteins to recognize and bind a host cell surface receptor, the angiotensin-converting enzyme 2 (ACE2), to gain host cell membrane fusion and viral entry [2-8]. Structurally, the SARS-CoV-2 S protein contains a receptor-binding domain (RBD) that holds a receptor-binding motif (RBM) in a "closed" configuration inaccessible by the host ACE2 receptor. Upon cleavage of the S protein by host proteases such as furin and the transmembrane protease/serine subfamily member 2 (TMPRSS2), the RBD undergoes a conformational change (from a "closed" to an "open" configuration) that enables "exposure" of RBM to host cell surface receptors [8-14].

In the absence of effective therapies for COVID-19, vaccination has become a key option to boost adaptive antibody responses against SARS-CoV-2 infections. One approach is to use a fragment of a SARS-CoV-2, typically a surface (such as the S spike) protein as antigens [15], in the hope that antibodies targeting the S protein may inhibit viral interaction with host ACE2 receptor to prevent viral entry [15]. In patients infected by SARS-CoV or SARS-CoV-2, neutralizing antibodies targeting the RBD or RBM region of respective S proteins were found [1, 3-7, 16-18]; and some of them indeed impaired RBD-ACE2 interaction [17] and viral entry [4, 16]. Intriguingly, a previous study revealed that antibodies against different epitopes of SARS-CoV S protein exhibited divergent effects: antibodies targeting RBM (residues 471-503) conferred protection; whereas antibodies targeting epitopes (e.g., residues 597-603) outside of the RBM region worsen the outcomes [19]. However, it was previously unknown how RBM-targeting antibodies would affect innate inflammatory responses to SARS-CoV-2 infections.

Recently emerging evidence suggests that ACE2 might also be expressed in innate immune cells such as human peripheral mononuclear cells (PBMCs) [20, 21] and murine macrophage-like RAW 264.7 cells [21]. Furthermore, human PBMCs produced several pro-inflammatory cytokines (e.g., TNF, IL-1β and IL-6) and chemokines (e.g., IL-8 and MIP-1(3) in response to SARS-CoV S protein stimulation [22].

Currently, extensive efforts have been made to produce vaccines against a surface fragment of a SARS-CoV-2, such as the spike protein, in order to boost protective antibody responses. Treatments and preventatives for COVID-19, including that caused by variants, are still urgently needed, and antibodies are one consideration.

SUMMARY OF THE INVENTION

A method of:

(i) inhibiting binding of severe acute respiratory syndrome coronavirus 2 (SARS-CoV-2) to an ACE2 receptor;

(ii) inhibiting a SARS-CoV-2 infection of, and/or SARS-CoV-2-induced GM-CSF production in, a cell comprising an ACE2 receptor; or (iii) treating a subject for a SARS-CoV-2 infection;

comprising administering an amount of an antibody, or a SARS-CoV-2 ACE2 Receptor Binding Motif (RBM)-binding fragment thereof, comprising

```
a) a heavy chain comprising one or more of:
                                          (SEQ ID NO: 21)
TDYMS

                                          (SEQ ID NO: 22)
AINSNGGTTYYPDTVKG

                                          (SEQ ID NO: 23)
QVKNGLDY

and/or a light chain comprising one or more of:
                                          (SEQ ID NO: 24)
RASQDISNYLN
                                          (SEQ ID NO: 25)
KTSRLHS
                                          (SEQ ID NO: 26)
QQGNTLPPT
or

b) a heavy chain comprising one or more of:
                                          (SEQ ID NO: 27)
SYYMS

                                          (SEQ ID NO: 28)
AINSNGGRTYYPDTVKG

                                          (SEQ ID NO: 29)
QGKNGLDY

and/or a light chain comprising one or more of:
                                          (SEQ ID NO: 30)
RASQDISNHLN

                                          (SEQ ID NO: 31)
YTSRLHS

                                          (SEQ ID NO: 32)
QQGKTLPPT
or

c) a heavy chain comprising one or more of:
                                          (SEQ ID NO: 33)
SSYMS

                                          (SEQ ID NO: 34)
AINNNGGTTYYPDTVKG
```

-continued (SEQ ID NO: 35)
QGKNGLDY and/or a light chain comprising one or more of:

(SEQ ID NO: 36)
RASQDIGNLLN (SEQ ID NO: 37)
YTSRLHS (SEQ ID NO: 38)
QQANTLPPT
or d) a heavy chain comprising one or more of:

(SEQ ID NO: 39)
SDYMS (SEQ ID NO: 40)
AINSNGGTTYYPDTVKG (SEQ ID NO: 41)
QGKNGMDY and/or a light chain comprising one or more of:

(SEQ ID NO: 42)
RASQDISNHLN (SEQ ID NO: 43)
YTSRLHS (SEQ ID NO: 44)
QQGKTLPPT.

A method of:

(i) inhibiting binding of severe acute respiratory syndrome coronavirus 2 (SARS-CoV-2) to an ACE2 receptor;

(ii) inhibiting a SARS-CoV-2 infection of, and/or SARS-CoV-2-induced GM-CSF production in, a cell comprising an ACE2 receptor; or (iii) treating a subject for a SARS-CoV-2 infection;

comprising administering an amount of a DNA or an mRNA (or a composition comprising such) encoding an antibody, or a SARS-CoV-2 ACE2 Receptor Binding Motif (RBM)-binding fragment thereof, which comprises:

a) a heavy chain comprising one or more of:

(SEQ ID NO: 21)
TDYMS (SEQ ID NO: 22)
AINSNGGTTYYPDTVKG (SEQ ID NO: 23)
QVKNGLDY and/or a light chain comprising one or more of:

(SEQ ID NO: 24)
RASQDISNYLN (SEQ ID NO: 25)
KTSRLHS (SEQ ID NO: 26)
QQGNTLPPT
or b) a heavy chain comprising one or more of:

(SEQ ID NO: 27)
SYYMS (SEQ ID NO: 28)
AINSNGGRTYYPDTVKG (SEQ ID NO: 29)
QGKNGLDY

-continued and/or a light chain comprising one or more of:

(SEQ ID NO: 30)
RASQDISNHLN (SEQ ID NO: 31)
YTSRLHS (SEQ ID NO: 32)
QQGKTLPPT
or c) a heavy chain comprising one or more of:

(SEQ ID NO: 33)
SSYMS (SEQ ID NO: 34)
AINNNGGTTYYPDTVKG (SEQ ID NO: 35)
QGKNGLDY and/or a light chain comprising one or more of:

(SEQ ID NO: 36)
RASQDIGNLLN (SEQ ID NO: 37)
YTSRLHS (SEQ ID NO: 38)
QQANTLPPT
or d) a heavy chain comprising one or more of:

(SEQ ID NO: 39)
SDYMS (SEQ ID NO: 40)
AINSNGGTTYYPDTVKG (SEQ ID NO: 41)
QGKNGMDY and/or a light chain comprising one or more of:

(SEQ ID NO: 42)
RASQDISNHLN (SEQ ID NO: 43)
YTSRLHS (SEQ ID NO: 44)
QQGKTLPPT.

BRIEF DESCRIPTION OF THE DRAWINGS

FIGS. 1(A)-1(E). Generation of the ACE2 receptor-binding domain (RBD) and receptor-binding motif (RBM) of SARS-CoV-2 spike protein. 1(A) Schematic diagram of SARS-CoV spike protein (S) and its ACE2 receptor binding domain (RBD) and motif (RBM). 1(B) Amino acid sequence of RBD and RBM of SARS-CoV and SARS-CoV2. RBM sequence is denoted by text in green; "@", denote residues in close contact with ACE2 (Lan, et al 2020). 1(C) SARS-CoV-2 spike protein RBD and RBM corresponding to amino acids 319-541 and 437-508 with an N-terminal histidine tag were expressed in *E. coli* BL21 (DE3) pLysS cells, and purified by differential centrifugation of inclusion bodies, urea solubilization and histidine-tag affinity chromatography. 1(D) some mutant strains of SARS-CoV-2 contain a point mutation (E484K) in the ACE2-binding motif (RBM). 1(E) SARS-CoV-2 RBM contains a sequence highly homologous to the epitope sequence (NDALYEYLRQ) (SEQ ID NO:2) of several anti-TN monoclonal antibodies (mAbs).

Highly purified extracellular domain of human ACE2 was immobilized on a sensor chip, and recombinant RBD or RBM was applied as analyte at various concentrations to estimate the dissociation equilibrium constant ($K_D$). 2(B), 2(C) Highly purified recombinant RBM was immobilized on the sensor chip, and recombinant human ACE2 (Panel 2(B)) or TN-specific mAbs (Panel 2(C)) were applied as analyte at various concentrations to assess the KD for RBM-ACE2 (Panel 2(B)) or RBM-mAb (Panel 2(C)) interactions. 2(D) highly purified recombinant RBM containing an E484K point mutation (RBM-m) was immobilized on the sensor chip, and TN-specific mAbs were applied as analyte at various concentrations to assess the KD for RBM-m-mAb interactions.

Figures 3A, 3B, 3C:
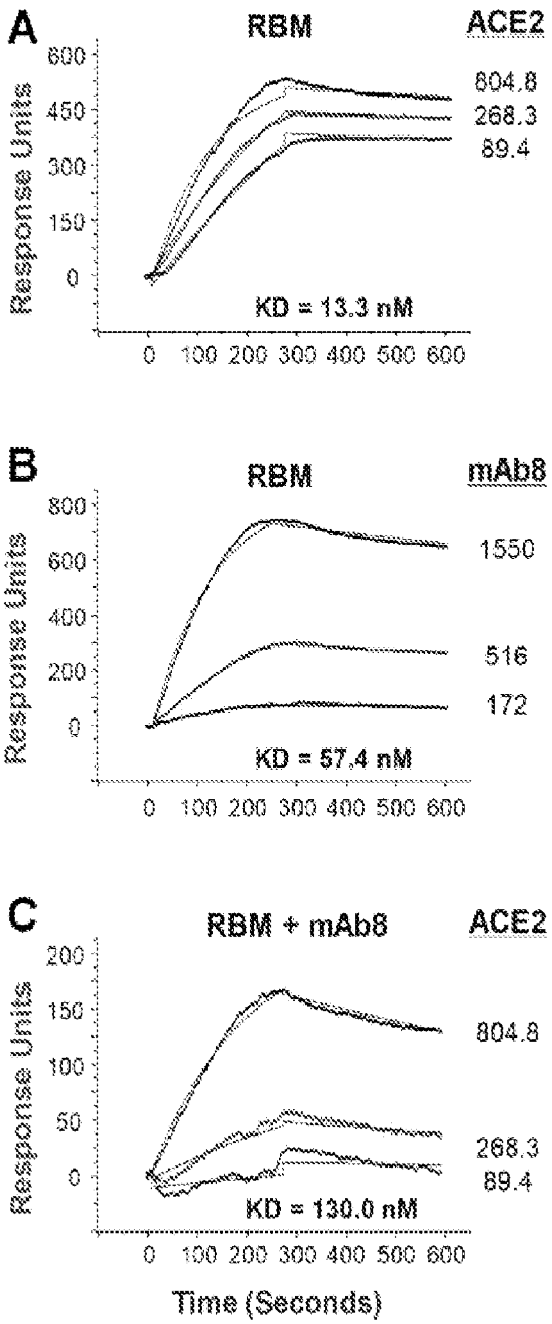

FIGS. 3(A)-3(C). RBM-reacting mAb interferes with RBM-ACE2 interaction. 3(A) Highly purified recombinant RBM was immobilized on the sensor chip, and recombinant human ACE2 was applied as analyte at various concentrations to assess the $K_D$ for RBM-ACE2 interaction. 3(B) After extensive washing, mAb8 was applied at indicated concentrations (Panel 3(B)), before ACE2 were re-applied to the RBM-conjugated sensor chip at identical concentrations (as in Panel 3(A)). The almost 10-fold increase in the $K_D$ (from 13.3 to 130.0 nM) and an almost 3-fold decrease (from 500 to 165) in the response units suggested that pre-treatment with mAb8 markedly inhibited RBM-ACE2 interaction ((3(C)).

Figure 4A:
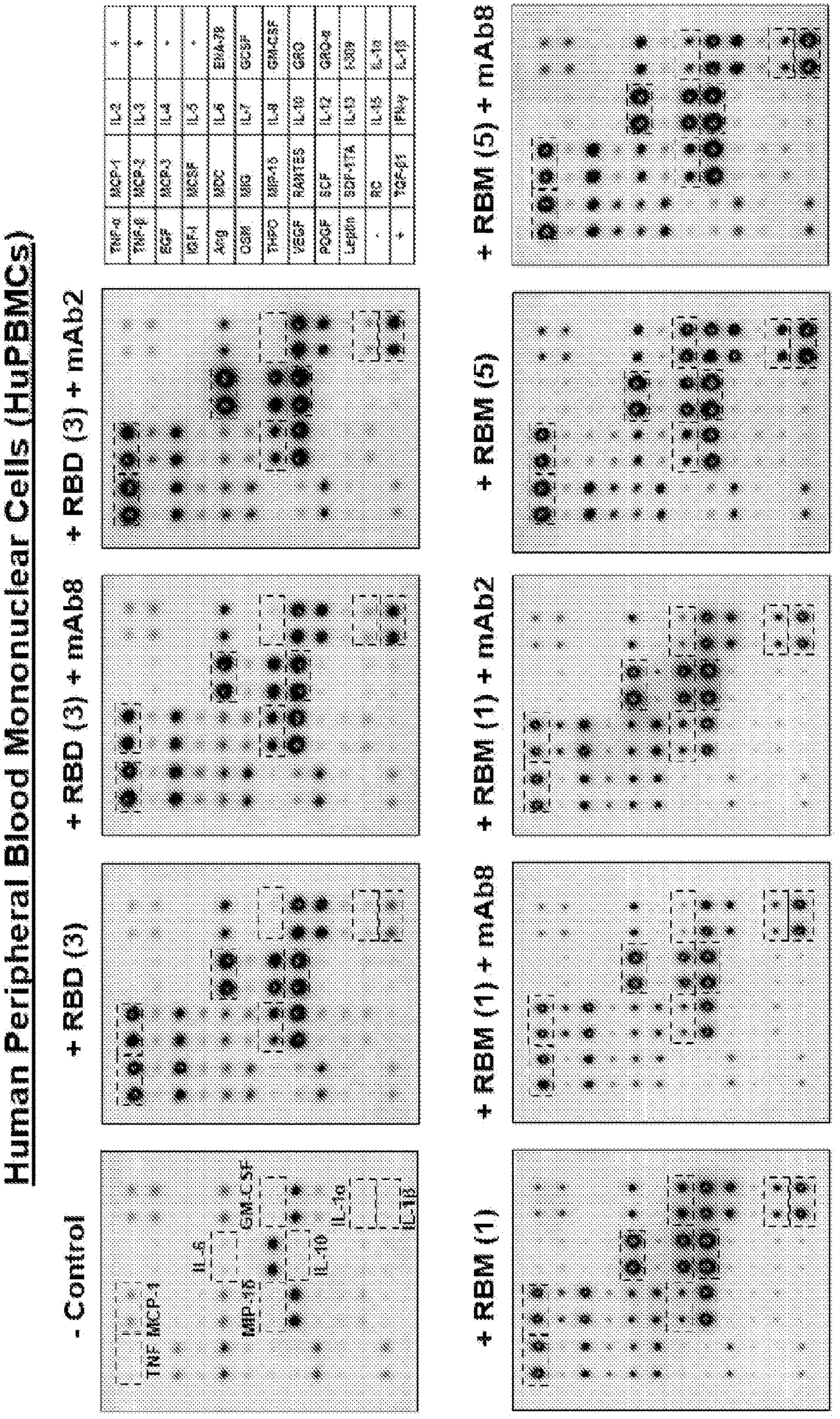
Figure 4B:
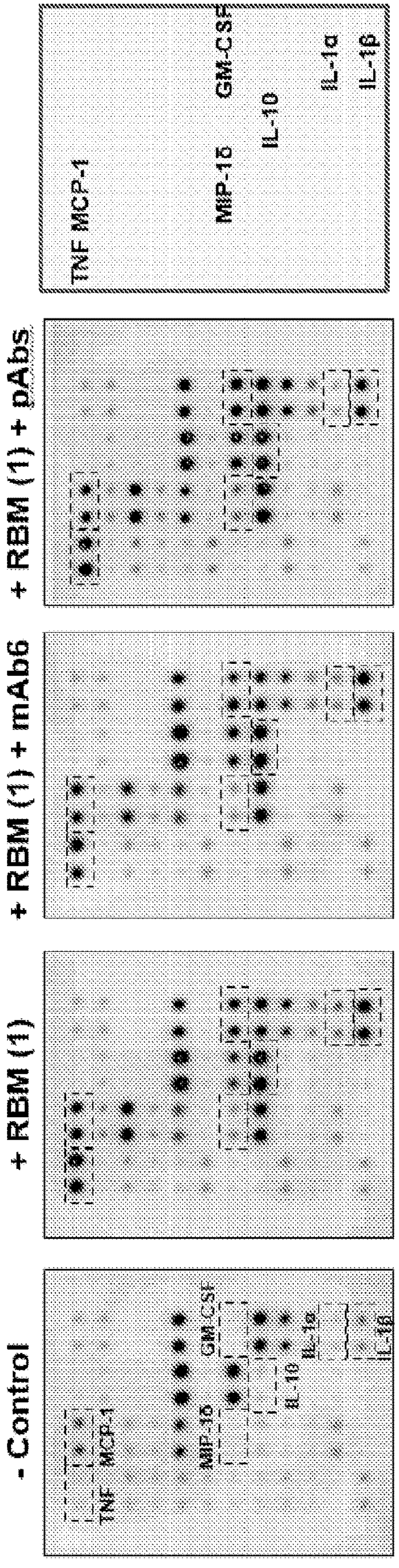
Figure 4C:
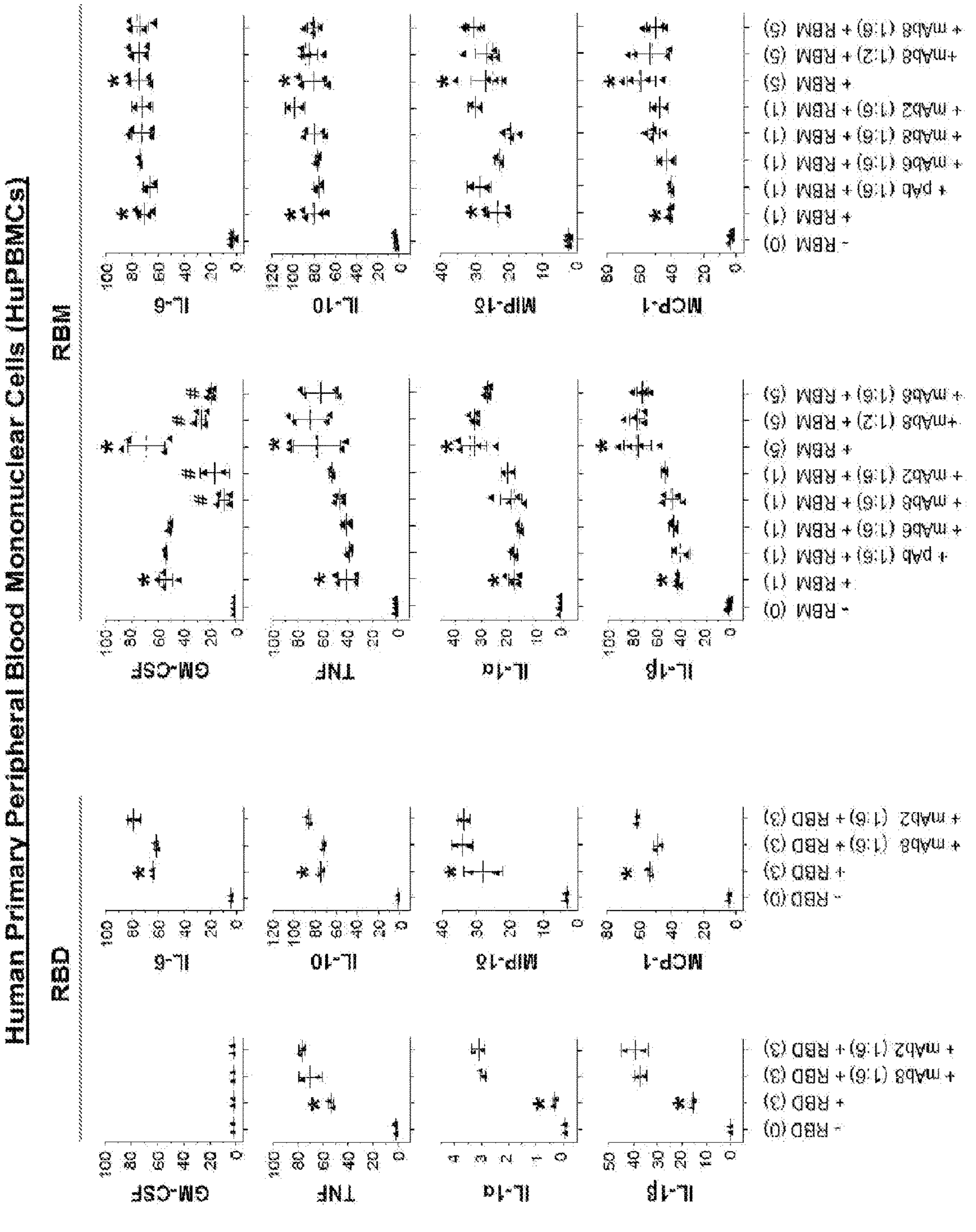

FIGS. 4(A)-4(C). RBM-reactive mAbs abrogated the RBM-induced secretion of GM-CSF in human peripheral blood mononuclear cells (PBMCs). Human peripheral blood mononuclear cells (HuPBMCs) were isolated from blood of healthy donors, and stimulated with recombinant RBD (3.0 μg/ml) or RBM (1.0 or 5.0 μg/ml) in the absence or presence of RBM-binding mAbs (mAb8, mAb2 or mAb6 at a molar ratio of 1:2 or 1:6) (4(A)) or irrelevant polyclonal antibodies (pAbs, 4(B)). At 16 h post stimulation, the extracellular concentrations of 42 different cytokines and chemokines were determined by Cytokine Antibody Arrays (4(C)), and normalized by the positive controls ("+") on respective membranes (4(A), 4(B)). *, $P<0.05$ versus negative controls ("−RBM" or "−R"); #, $P<0.05$ versus positive controls ("+RBM" or "+R") at respective concentrations.

Figure 5A:
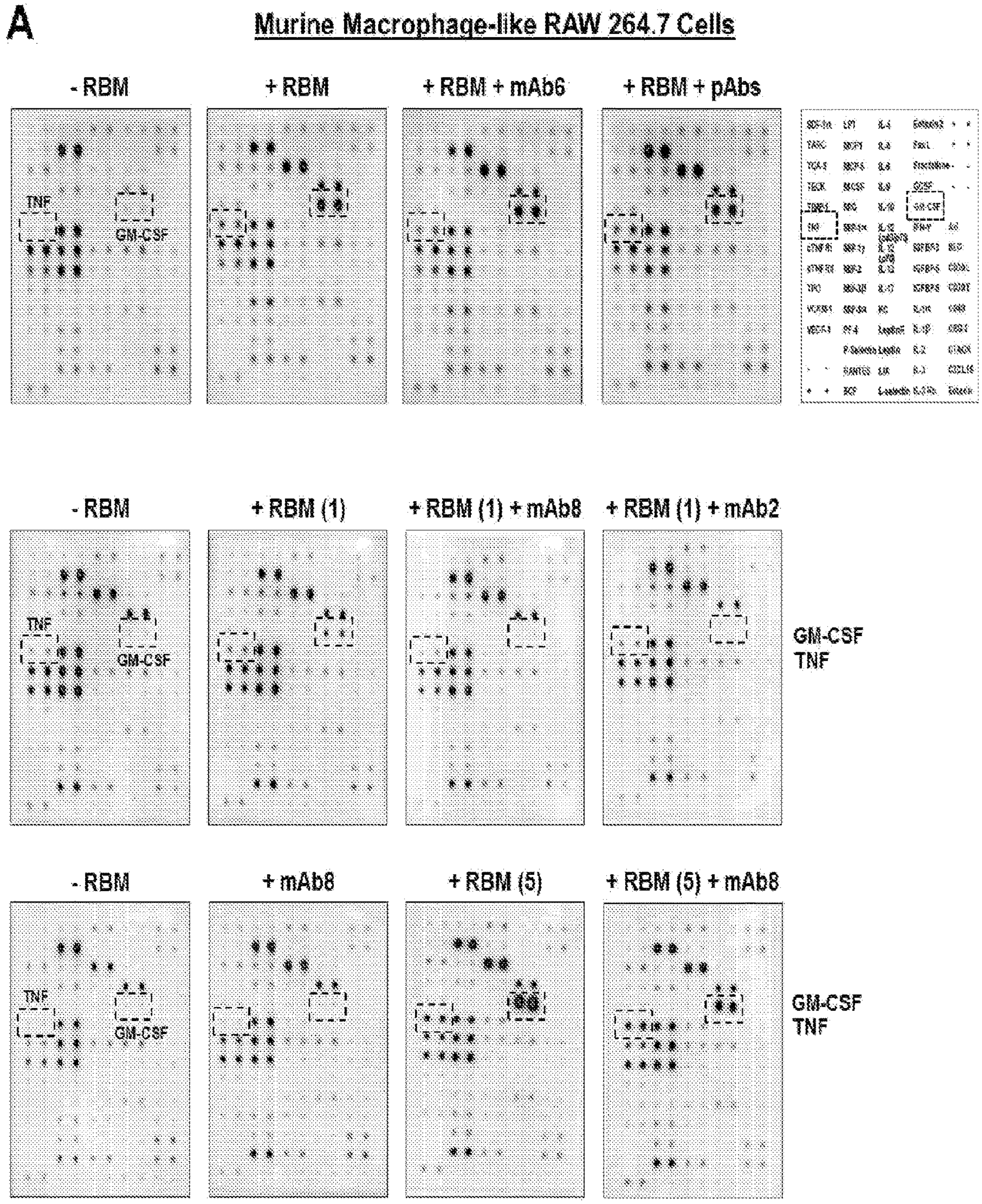
Figures 5B, 5C:
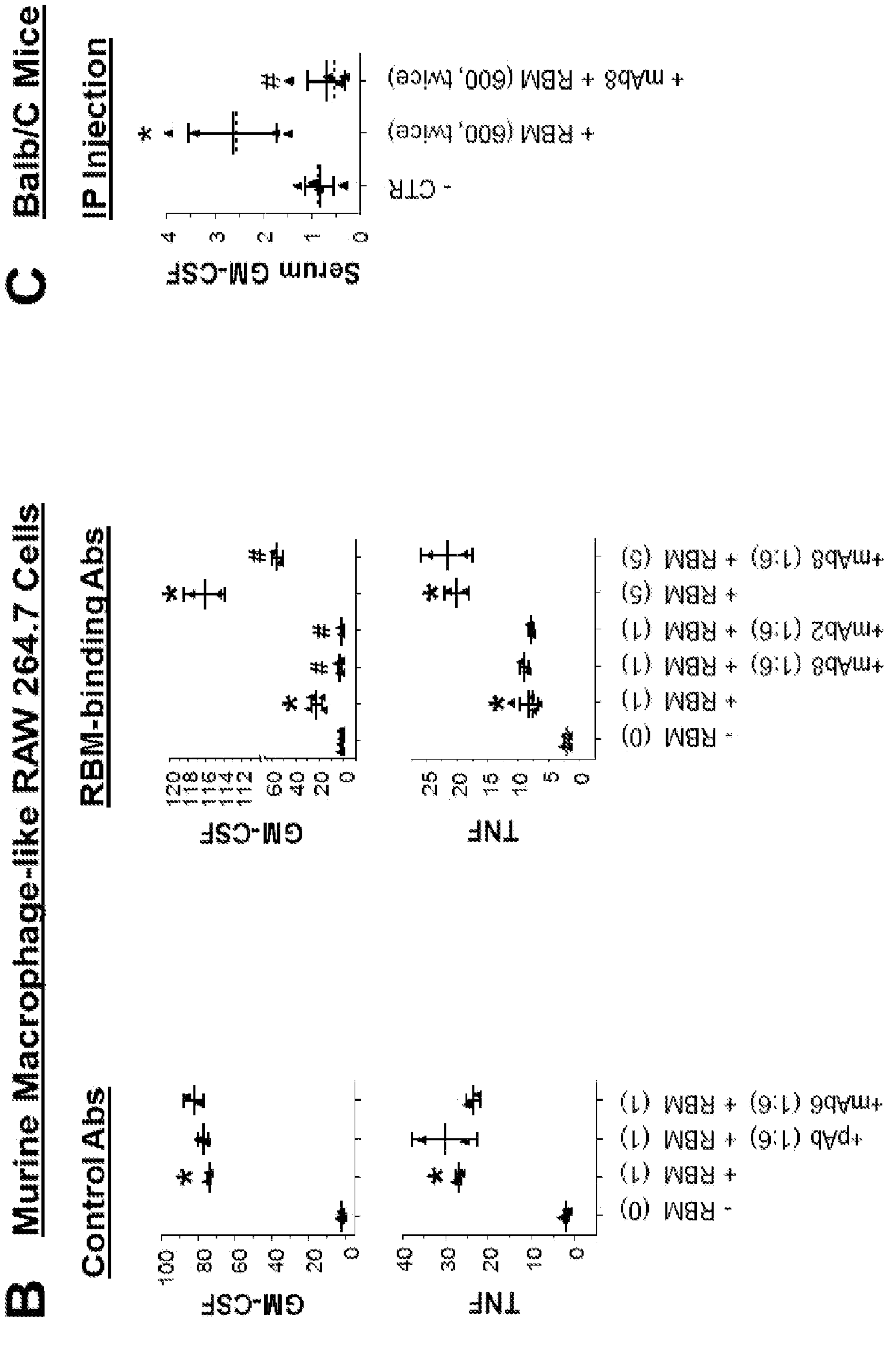

FIGS. 5(A)-5(C). RBM-reactive mAbs blocked the RBM-induced GM-CSF secretion in murine macrophage-like RAW 264.7 cells. Murine macrophage-like RAW 264.7 cells were stimulated with recombinant RBM (1.0 or 5.0 μg/ml) either alone or in the presence of three different RBM-binding mAbs (at a molar ratio of 1:6) or irrelevant polyclonal antibodies (pAbs, 5(A)), and extracellular concentrations of 62 cytokines and chemokines were measured by Cytokine Antibody Arrays at 16 h post stimulation (5(B)). *, $P<0.05$ versus negative controls ("−RBM" or "−R"); #, $P<0.05$ versus positive controls ("+RBM" or "+R") at respective concentrations. 5(C) RBM-reactive mAb8 attenuated the RBM-induced GM-CSF induction in vivo. Male Balb/C mice were intraperitoneally and repetitively administered with recombinant RBM (at t=0 and t=12 h) at a higher dose (600 μg/mouse) either alone or in combination with a RBM-binding mAb (mAb8, 2.0 mg/mouse) at the same time. At 16 h post the initial RBM administration, animals were euthanized to harvest blood to measure serum levels of cytokines and chemokines using Cytokine Antibody Arrays (n=4). *, $P<0.05$ versus a negative control ("+Saline"). #, $P<0.05$ versus a positive control ("+RBM" alone).

Figure 6A:
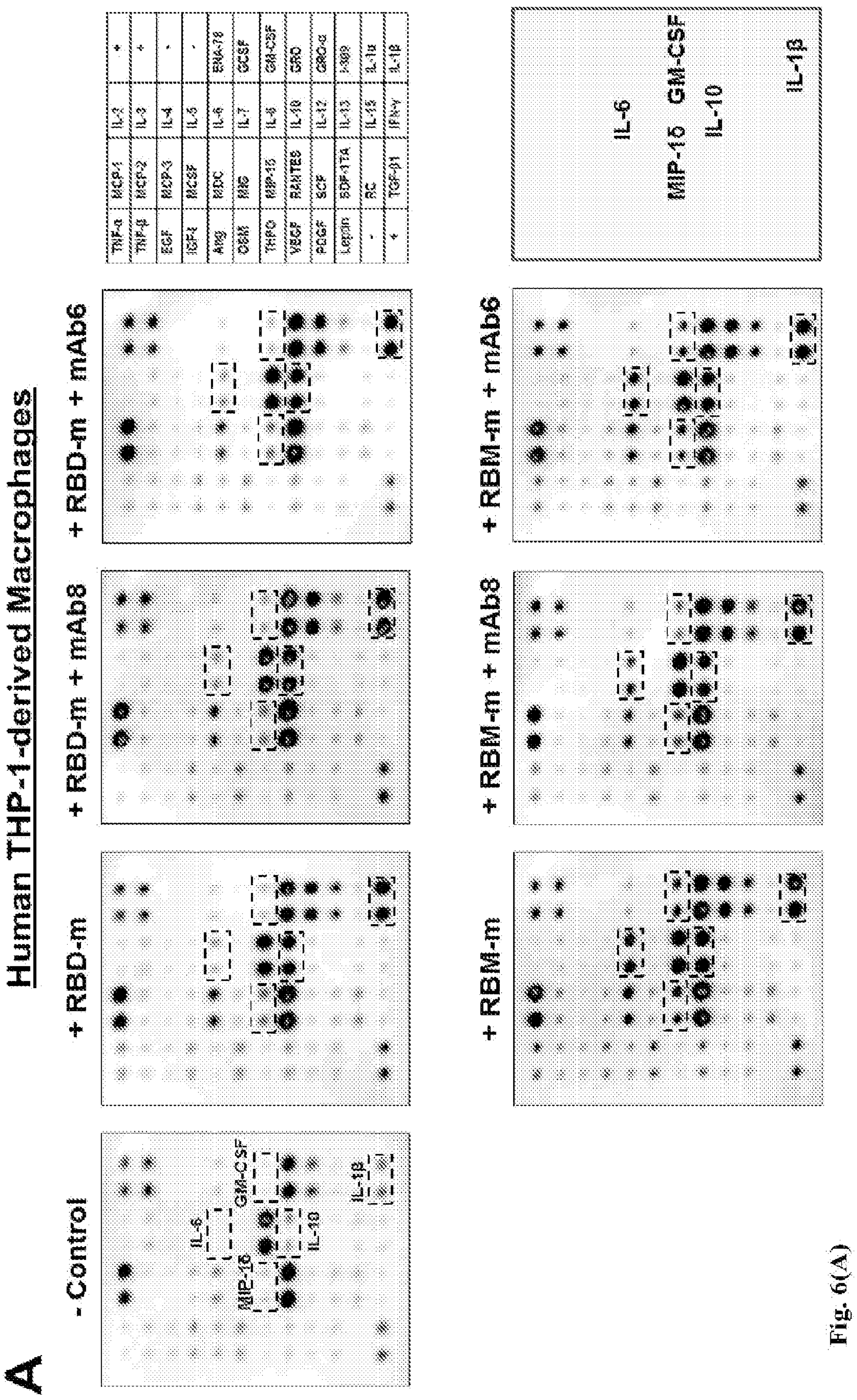
Figure 6B:
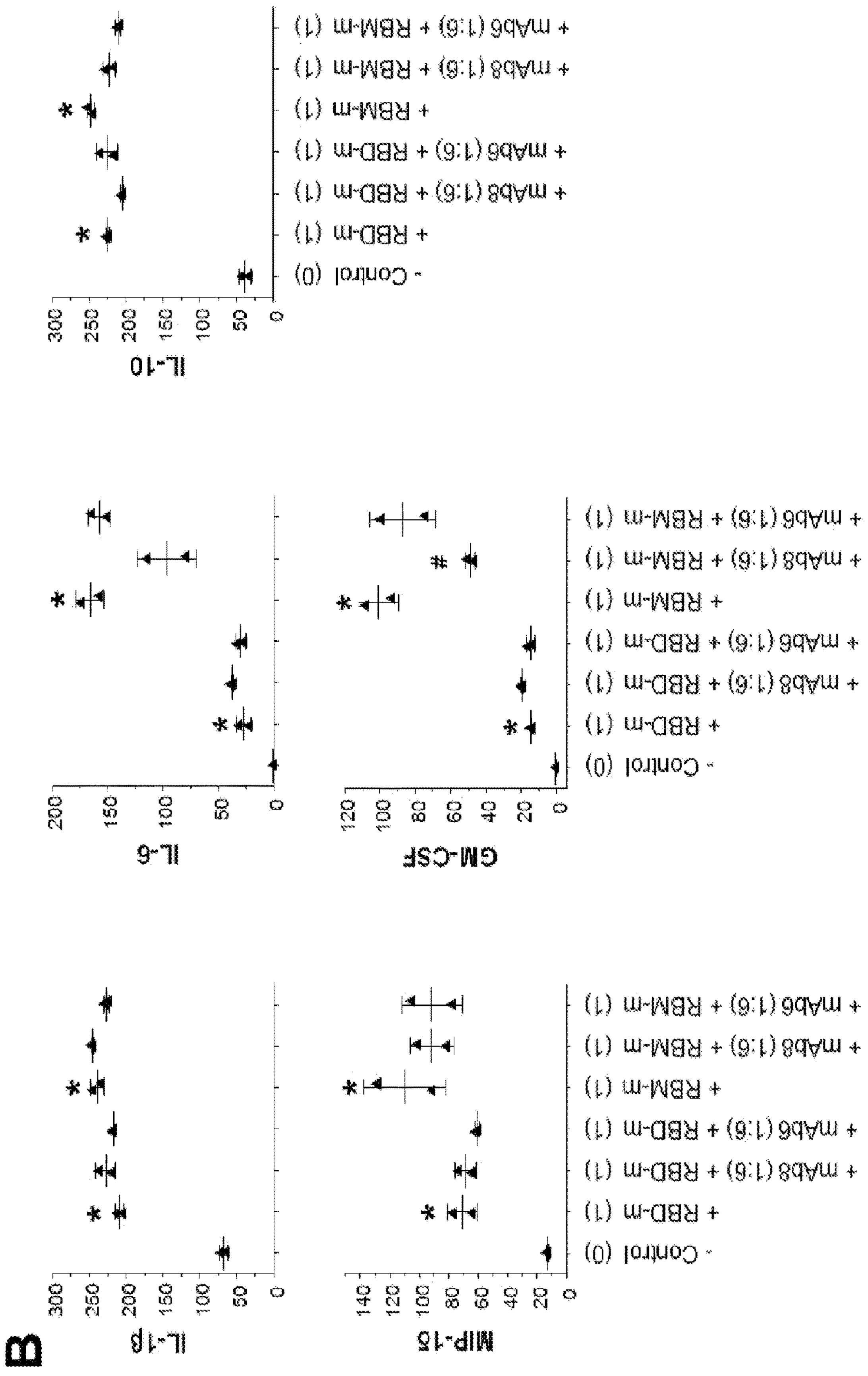
Figure 6C:
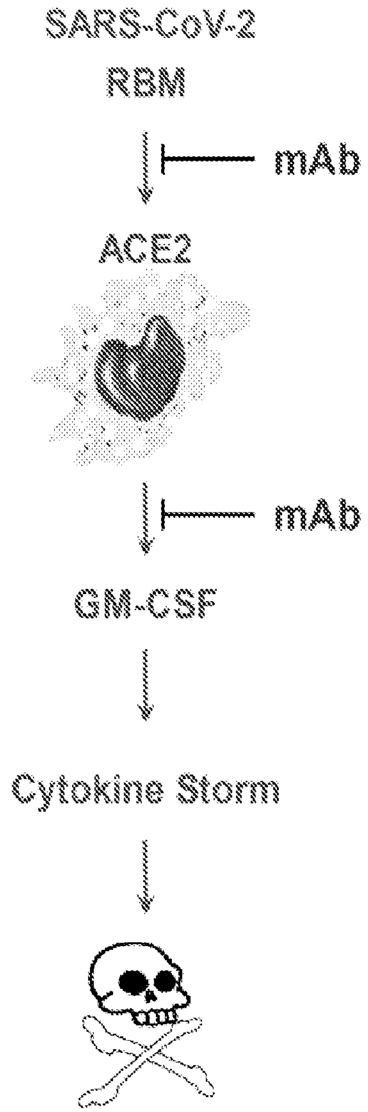

FIGS. 6(A)-6(C). RBM-reactive mAbs blocked the RBM-induced GM-CSF secretion in human THP-1 cells. Human THP-1 monocytes were differentiated into macrophages by phorbol 12-myristate 13-acetate (PMA, 20 ng/ml for 72 h), and then stimulated with recombinant RBD-m or RBM-m containing an E484K point mutation (1.0 μg/ml) in the absence or presence of two different mAbs (at a molar ration of 1:6) for 16 h. The extracellular concentrations of 42 different cytokines and chemokines were determined by Cytokine Antibody Arrays (6(A), and normalized by the positive controls ("+") on respective membranes (6(B)). *, $P<0.05$ versus negative controls ("−RBM" or "−R"); #, $P<0.05$ versus positive controls ("+RBM-m" or "+RBD-m") at respective concentrations. 6(C) Proposed model for the mAb-mediated inhibition of SARS-CoV-2 RBM-induced GM-CSF secretion. SARS-CoV-2 RBM may bind ACE2 receptor to trigger the specific secretion of GM-CSF by macrophages and monocytes. Monoclonal antibodies capable of interrupting RBM-ACE2 interaction impairs the RBM-induced GM-CSF secretion without affecting the RBM-induced release of other pro-inflammatory (e.g., IL-1β, IL-6, TNF) and anti-inflammatory cytokines (e.g., IL-10) or chemokines (MCP-1 and MIP-1δ).

FIG. 7. Amino acid sequence of human tetranectin protein (SEQ ID NO:1) containing the epitope sequence (underlined text, SEQ ID NO:2) for the monoclonal antibodies.

FIG. 8. Epitope sequence (SEQ ID NO:2) for the monoclonal antibodies.

FIG. 9. Amino acid sequence of the receptor binding domain (RBD, residues 319-541) (SEQ ID NO:45) of SARS-CoV (full length SEQ ID NO:46) and receptor-binding motif (RBM, residues 437-508) (SEQ ID NO:3) of SARS-CoV-2 viruses (full length SEQ ID NO:47).

FIG. 10. Homology between a sequence in the RBM of SARS-CoV-2 (SEQ ID NO:4) and the epitope sequence (SEQ ID NO:2) for mAbs of the disclosure. Exemplary antibodies include 27B12 (mAb8, SEQ ID NO 5-8, 21, 22), 25B2 (mAb6, SEQ ID NO 9-12, 21, 22), 23F6 (mAb5, SEQ ID NO 13-16, 21, 22), and 18B1 (mAb2, SEQ ID NO 17-20, 21, 22).

FIG. 11. CDR sequences and dissociation equilibrium constant ($K_D$) for all antibodies.

FIG. 12. Antibody amino acid sequences, including signal peptides.

DETAILED DESCRIPTION OF THE INVENTION

The disclosures of all publications, patents, patent application publications and books referred to herein, are hereby incorporated by reference in their entirety into the subject application to more fully describe the art to which the subject invention pertains.

Here are disclosed RBM-binding monoclonal antibodies (mAbs) that competitively inhibit the interaction of RBM of SARS-CoV-2 with human ACE2, and also specifically block the RBM-induced GM-CSF secretion in both human monocyte and murine macrophage cultures.

A method is provided of:

(i) inhibiting binding of severe acute respiratory syndrome coronavirus 2 (SARS-CoV-2) to an ACE2 receptor;

(ii) inhibiting a SARS-CoV-2 infection of, and/or SARS-CoV-2-induced GM-CSF production in, a cell comprising an ACE2 receptor; or (iii) treating a subject for a SARS-CoV-2 infection;

comprising administering an amount of an antibody, or a SARS-CoV-2 ACE2 Receptor Binding Motif (RBM)-binding fragment thereof, comprising a) a heavy chain comprising one or more of:

(SEQ ID NO: 21)
TDYMS (SEQ ID NO: 22)
AINSNGGTTYYPDTVKG (SEQ ID NO: 23)
QVKNGLDY and/or a light chain comprising one or more of:

(SEQ ID NO: 24)
RASQDISNYLN (SEQ ID NO: 25)
KTSRLHS (SEQ ID NO: 26)
QQGNTLPPT or b) a heavy chain comprising one or more of:

(SEQ ID NO: 27)
SYYMS (SEQ ID NO: 28)
AINSNGGRTYYPDTVKG (SEQ ID NO: 29)
QGKNGLDY and/or a light chain comprising one or more of:

(SEQ ID NO: 30)
RASQDISNHLN (SEQ ID NO: 31)
YTSRLHS (SEQ ID NO: 32)
QQGKTLPPT or c) a heavy chain comprising one or more of:

(SEQ ID NO: 33)
SSYMS (SEQ ID NO: 34)
AINNNGGTTYYPDTVKG (SEQ ID NO: 35)
QGKNGLDY and/or a light chain comprising one or more of:

(SEQ ID NO: 36)
RASQDIGNLLN (SEQ ID NO: 37)
YTSRLHS (SEQ ID NO: 38)
QQANTLPPT or d) a heavy chain comprising one or more of.

(SEQ ID NO: 39)
SDYMS (SEQ ID NO: 40)
AINSNGGTTYYPDTVKG (SEQ ID NO: 41)
QGKNGMDY and/or a light chain comprising one or more of:

(SEQ ID NO: 42)
RASQDISNHLN (SEQ ID NO: 43)
YTSRLHS

-continued (SEQ ID NO: 44)
QQGKTLPPT.

In embodiments, the antibody, or antigen-binding fragment thereof, binds to a sequence NDALYEYLRQ (SEQ ID NO:2) of a human tetranectin or a sequence in RBM domain of SARS-CoV-2 (SEQ ID NO: 3 and/or 4).

In embodiments, the antibody, or antigen-binding fragment thereof, comprises a heavy chain comprising one or more of:

(SEQ ID NO: 21)
TDYMS (SEQ ID NO: 22)
AINSNGGTTYYPDTVKG (SEQ ID NO: 23)
QVKNGLDY and/or a light chain comprising one or more of:

(SEQ ID NO: 24)
RASQDISNYLN (SEQ ID NO: 25)
KTSRLHS (SEQ ID NO: 26)
QQGNTLPPT.

In embodiments, the antibody, or antigen-binding fragment thereof, comprises a heavy chain comprising one or more of:

(SEQ ID NO: 27)
SYYMS (SEQ ID NO: 28)
AINSNGGRTYYPDTVKG (SEQ ID NO: 29)
QGKNGLDY and/or a light chain comprising one or more of:

(SEQ ID NO: 30)
RASQDISNHLN (SEQ ID NO: 31)
YTSRLHS (SEQ ID NO: 32)
QQGKTLPPT.

In embodiments, the antibody, or antigen-binding fragment thereof, comprises a heavy chain comprising one or more of:

(SEQ ID NO: 33)
SSYMS (SEQ ID NO: 34)
AINNNGGTTYYPDTVKG (SEQ ID NO: 35)
QGKNGLDY and/or a light chain comprising one or more of:

(SEQ ID NO: 36)
RASQDIGNLLN (SEQ ID NO: 37)
YTSRLHS (SEQ ID NO: 38)
QQANTLPPT.

In embodiments, the antibody, or antigen-binding fragment thereof, comprises a heavy chain comprising one or more of:

```
                                    (SEQ ID NO: 39)
SDYMS

                                    (SEQ ID NO: 40)
AINSNGGTTYYPDTVKG

                                    (SEQ ID NO: 41)
QGKNGMDY

and/or a light chain comprising one or more of:
                                    (SEQ ID NO: 42)
RASQDISNHLN

                                    (SEQ ID NO: 43)
YTSRLHS

                                    (SEQ ID NO: 44)
QQGKTLPPT.
```

In embodiments, the antibody, or antigen-binding fragment thereof, comprises framework regions of the light chain and/or the heavy chain which are human framework regions, or have 85% or more identity thereto.

In embodiments, framework regions of the light chain and/or the heavy chain are human framework regions.

In embodiments, the antibody or antigen-binding fragment thereof binds to a sequence NDALYEYLRQ (SEQ ID NO:2) of a human tetranectin or a sequence in RBM domain of SARS-CoV-2 (SEQ ID NO: 3 and/or 4) with an affinity of 3.0 nM KD or stronger.

In embodiments, the antibody or antigen-binding fragment thereof binds to a sequence NDALYEYLRQ (SEQ ID NO:2) of a human tetranectin or a sequence in RBM domain of SARS-CoV-2 (SEQ ID NO: 3 and/or 4) with an affinity of 2.0 nM KD or stronger.

In embodiments, the antibody or antigen-binding fragment thereof has a human sequence Fc region.

In embodiments, the antibody or fragment thereof is chimeric or humanized.

In embodiments, the antibody or fragment thereof is selected from the group consisting of a monoclonal antibody, an scFv, an Fab fragment, an Fab' fragment, an F(ab)' fragment and a bispecific antibody.

In embodiments, the antibody is a humanized antibody and is an IgG1(λ) or an IgG2(λ).

In embodiments, the method inhibits interaction between an ACE2 Receptor Binding Motif (RBM) of a spike protein of a SARS-CoV-2 and an ACE2 Receptor.

In embodiments, the antibody or antigen-binding fragment thereof binds to an ACE2 Receptor Binding Motif (RBM) of a spike protein of a SARS-CoV-2 with an affinity of 2.0 nM KD or stronger.

In embodiments, the antibody or antigen-binding fragment thereof binds to an ACE2 Receptor Binding Motif (RBM) of a spike protein of a SARS-CoV-2 with an affinity of 10.0 nM KD or stronger.

In embodiments, the antibody or antigen-binding fragment thereof binds to an ACE2 Receptor Binding Motif (RBM) of a spike protein of a SARS-CoV-2 with an affinity of 20.0 nM KD or stronger.

A method is also provided of:

(i) inhibiting binding of severe acute respiratory syndrome coronavirus 2 (SARS-CoV-2) to an ACE2 receptor;

(ii) inhibiting a SARS-CoV-2 infection of, and/or SARS-CoV-2-induced GM-CSF production in, a cell comprising an ACE2 receptor; or (iii) treating a subject for a SARS-CoV-2 infection;

comprising administering an amount of a DNA or an mRNA encoding an antibody, or a SARS-CoV-2 ACE2 Receptor Binding Motif (RBM)-binding fragment thereof, which comprises:

```
a) a heavy chain comprising one or more of:
                                    (SEQ ID NO: 21)
TDYMS

                                    (SEQ ID NO: 22)
AINSNGGTTYYPDTVKG

                                    (SEQ ID NO: 23)
QVKNGLDY

and/or a light chain comprising one or more of:
                                    (SEQ ID NO: 24)
RASQDISNYLN

                                    (SEQ ID NO: 25)
KTSRLHS

                                    (SEQ ID NO: 26)
QQGNTLPPT
or

b) a heavy chain comprising one or more of:
                                    (SEQ ID NO: 27)
SYYMS

                                    (SEQ ID NO: 28)
AINSNGGRTYYPDTVKG

                                    (SEQ ID NO: 29)
QGKNGLDY

and/or a light chain comprising one or more of:
                                    (SEQ ID NO: 30)
RASQDISNHLN

                                    (SEQ ID NO: 31)
YTSRLHS

                                    (SEQ ID NO: 32)
QQGKTLPPT
or

c) a heavy chain comprising one or more of:
                                    (SEQ ID NO: 33)
SSYMS

                                    (SEQ ID NO: 34)
AINNNGGTTYYPDTVKG

                                    (SEQ ID NO: 35)
QGKNGLDY

and/or a light chain comprising one or more of:
                                    (SEQ ID NO: 36)
RASQDIGNLLN

                                    (SEQ ID NO: 37)
YTSRLHS

                                    (SEQ ID NO: 38)
QQANTLPPT
or

d) a heavy chain comprising one or more of:
                                    (SEQ ID NO: 39)
SDYMS

                                    (SEQ ID NO: 40)
AINSNGGTTYYPDTVKG
```

-continued (SEQ ID NO: 41)
QGKNGMDY and/or a light chain comprising one or more of:

(SEQ ID NO: 42)
RASQDISNHLN (SEQ ID NO: 43)
YTSRLHS (SEQ ID NO: 44)
QQGKTLPPT.

In embodiments, nucleic acid described herein is a cDNA. In embodiments, nucleic acid described herein is a DNA. In embodiments, nucleic acid described herein is an RNA. In embodiments, nucleic acid described herein is an isolated nucleic acid.

Also provided is a host cell comprising one or more of the nucleic acids described herein. In embodiments, the host cell is a mammalian cell. In embodiments, the host cell is derived from a mammalian cell. In embodiments, the host cell is a CHO, NS0, Sp2/0, HEK293, or PER.C6 cell.

Also provided is an antibody or fragment thereof described herein, linked or conjugated to a therapeutic agent, an imaging agent or a detectable marker. In embodiments, the therapeutic agent is an anti-viral drug, cytotoxic drug, an anti-inflammatory drug, a radioactive isotope, an immunomodulator, or a second antibody.

In embodiments, the subject is mammalian. In embodiments, the subject is human. In embodiments, the subject is administered the antibody or fragment thereof prophylactically. In embodiments, the subject is administered the antibody or fragment thereof when it is suspected by the treatment administrator that the subject may experience the pathology (e.g. COVID-19, etc.). In embodiments, the subject being administered the antibody or fragment thereof is already experiencing the disease state/has the pathology. In an embodiment, the subjected has tested positive on a SARS-CoV-2 PCR or antigen test.

Also provided is an isolated anti-RBM of a SARS-CoV-2 antibody or antibody fragment that cross-competes for specific binding to a sequence NDALYEYLRQ (SEQ ID NO:2) in a human tetranectin with a reference antibody or antibody fragment, said reference antibody or antibody fragment comprising a heavy chain variable region comprising the CDR sequences set forth in SEQ ID NOs:21-23, SEQ ID NOs:27-29, SEQ ID NOs:33-35 or SEQ ID NOs:39-41; and/or a light chain variable region comprising the CDR sequences set forth in SEQ ID NOs:24-26, SEQ ID NOs: 30-32, SEQ ID NOs:36-38, or SEQ ID NOs:42-44. In embodiments, the heavy chain variable region comprises an amino acid sequence comprising at least 85% sequence identity to SEQ ID NO:4 or SEQ ID NO:8 or SEQ ID NO:12 or SEQ ID NO:16. In embodiments, the light chain variable region comprises an amino acid sequence comprising at least 85% sequence identity to SEQ ID NO:6 or SEQ ID NO:10 or SEQ ID NO:14 or SEQ ID NO:18.

Also provided is a pharmaceutical composition comprising an effective amount of the antibody or antibody fragment as described herein, and a pharmaceutically acceptable carrier or excipient.

Also provided is use of an effective amount of an antibody or fragment thereof as described herein for the manufacture of a medicament for treating or preventing a disease or condition that is associated with COVID-19 in a subject.

In embodiments of the antibodies and fragments described herein, the framework regions of the light chain and the heavy chain are human framework regions, or have 85% or more identify thereto.

In embodiments of the antibodies and fragments described herein, the framework regions of the light chain and the heavy chain are human framework regions.

In embodiments, the isolated antibody or antigen-binding fragment thereof has a human sequence Fc region.

In embodiments, the isolated antibody or antigen-binding fragment thereof the antibody or fragment thereof is chimeric or humanized.

In embodiments, the isolated antibody or antigen-binding fragment thereof the antibody or fragment thereof is selected from the group consisting of a monoclonal antibody, an scFv, an Fab fragment, an Fab' fragment, and an F(ab)' fragment. It is noted that while an scFv is not strictly a fragment of an antibody, rather it is a fusion protein, herein a fragment of an antibody includes an scFv unless otherwise excluded.

A host cell is provided comprising one or more of the nucleic acids described herein.

An antibody or fragment thereof described herein is provided linked or conjugated to a therapeutic agent.

In embodiments, the therapeutic agent is a cytotoxic drug, a radioactive isotope, an immunomodulator, or a second antibody.

A method of detecting a SARS-CoV-2 in a subject is provided comprising administering an amount of an antibody or fragment thereof as described herein, having a detectable marker conjugated thereto, in an amount effective to label an RBM of a SARS-CoV-2 and then detecting the presence of bound detectable marker in the subject, thereby detecting a SARS-CoV-2 in a subject. In embodiments, the label is detected by imaging. In embodiments, the cell is a pulmonary cell.

In embodiments, the anti-RBM of a SARS-CoV-2 antibody or fragment thereof, comprises (i) a VH framework comprising the framework sequence of human germline IGHV1-2*02, IGHV1-2*04, IGHV1-2*05, IGHV1-18*04, IGHV1-69-2*01, IGHV1-46*01, IGHD5-12*01, IGHD5-24*01, IGHD6-25*01, IGHJ3*01, IGHJ4*01, IGHJ4*03, IGHJ6*01, IGHJ6*02 and/or (ii) a VL framework comprising the framework sequence of human germline IGKV1-13*02, IGKV1-27*01, IGKV3-7*02, IGKV4-1*01, IGKV1D-13*02, IGKV3D-7*01, IGKJ1*01, IGKJ2*01, IGKJ4*01, IGKJ4*02.

In embodiments, the anti-RBM of a SARS-CoV-2 antibody or fragment thereof is a monoclonal antibody.

In embodiments, the anti-RBM of a SARS-CoV-2 antibody or fragment thereof is a recombinant antibody.

In embodiments, the anti-RBM of a SARS-CoV-2 antibody or fragment thereof has a human framework region.

In embodiments, the anti-RBM of a SARS-CoV-2 or fragment thereof has a human constant region.

In embodiments, the anti-RBM of a SARS-CoV-2 antibody is provided. In embodiments, the fragment of the antibody is provided.

In embodiments, the anti-RBM of a SARS-CoV-2 antibody fragment is an Fab, F(ab)2 or scFv.

A method of inhibiting a SARS-CoV-2-associated cytokine storm in a subject is provided comprising administering to a subject infected with a SARS-CoV-2 an amount of an antibody or antibody fragment as described herein effective to reduce or prevent a SARS-CoV-2-associated cytokine storm in a subject.

As used herein, the term “antibody” refers to an intact antibody, i.e. with complete Fc and Fv regions. “Fragment” refers to any portion of an antibody, or portions of an antibody linked together, such as, in non-limiting examples, a Fab, F(ab)2, a single-chain Fv (scFv), which is less than the whole antibody but which is an antigen-binding portion and which competes with the intact antibody of which it is a fragment for specific binding. In this case, the antigen is sequence found in the RBM of SARS-Co-V-2, as described elsewhere herein.

Such fragments can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment, single-chain antibody (scFv), (a variable domain light chain (VL) and a variable domain heavy chain (VH) linked via a peptide linker. In an embodiment, the scFv comprises a variable domain framework sequence having a sequence identical to a human variable domain FR1, FR2, FR3 or FR4. In an embodiment, the scFv comprises a linker peptide from 5 to 30 amino acid residues long. In an embodiment, the scFv comprises a linker peptide comprising one or more of glycine, serine and threonine residues.

In an embodiment the linker of the scFv is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989), each of which are hereby incorporated by reference in their entirety). As used herein, the term “polypeptide” encompasses native or artificial proteins, protein fragments and polypeptide analogs of a protein sequence. A polypeptide may be monomeric or polymeric. As used herein, an Fd fragment means an antibody fragment that consists of the VH and CH1 domains; an Fv fragment consists of the V1 and VH domains of a single arm of an antibody; and a dAb fragment (Ward et al., Nature 341:544-546 (1989) hereby incorporated by reference in its entirety) consists of a VH domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term “monoclonal antibody” as used herein refers to an antibody member of a population of substantially homogeneous antibodies, i.e., the individual antibodies comprising the population are identical except for possible mutations, e.g., naturally occurring mutations, that may be present in minor amounts. Thus, the modifier “monoclonal” indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus, an identified monoclonal antibody can be produced by non-hybridoma techniques, e.g. by appropriate recombinant means once the sequence thereof is identified.

In an embodiment of the inventions described herein, the antibody is isolated. As used herein, the term “isolated antibody” refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not occur in nature absent the hand of man.

In an embodiment the antibody is humanized. “Humanized” forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) (or CDR) of the recipient are replaced by residues from a HVR (or CDR) of a non-human species (donor antibody) such as mouse, rat, rabbit, or nonhuman primate having the desired specificity, affinity, and/or capacity. In an embodiment, the antibody has 1, 2, 3, 4, 5, or all 6 CDR1-3 of both the heavy and light chain of the antibodies described herein. In a preferred embodiment, framework (FR) residues of the murine mAb are replaced with corresponding human immunoglobulin variable domain framework (FR) residues. These may be modified further in embodiments to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all, or in embodiments substantially all, of the hypervariable loops correspond to those of a non-human immunoglobulin, and all, or in embodiments substantially all, of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are well known and are described in, for example, U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. A number of “humanized” antibody molecules comprising an antigen-binding site derived from a nonhuman immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more, or all, CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

The term "$K_d$", as used herein, is intended to refer to the dissociation constant of an antibody-antigen interaction. One way of determining the $K_d$ or binding affinity of antibodies to the specified antigen is by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of a fragment of an antibody can be determined, for example, by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiimide hydrochloride (EDC) and N-hydroxysuccinimide (NHS) according to the supplier's instructions. The antigen can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_d$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any antigen. Other protocols known in the art may also be used. For example, ELISA.

An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a given sequence in RBM of SARS-CoV-2 and/or tetranectin is an antibody that binds this epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibody subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) (or CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). There are CDRs 1, 2, and 3 for each of the heavy and light chains. Chothia refers instead to the location of the structural loops (Chothia and Lesk, J. Mol. Biol. 196:901-917 (1987)). The AbM HVRs represent a compromise between the Kabat HVRs and Chothia structural loops and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua et al, 2006; Yeung et al, 2009). In an embodiment, the Fc domain has the same sequence as a human IgG1 Fc domain.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed.

Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g. 2-[2-[3,5-bis(2-hydroxyethoxy) oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

In embodiments, the variable regions disclosed herein are not modified. In embodiments, the invention encompasses modifications to the variable regions disclosed herein. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to the herein identified sequence in the RBM of SARS-CoV-2. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |

TABLE 1-continued

Amino Acid Substitutions

| Original Residue | Conservative Substitutions | Exemplary Substitutions |
|---|---|---|
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

A modification or mutation may also be made in a framework region or constant region to increase the half-life of an antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In an embodiment, an antibody described herein is recombinantly produced. In an embodiment, the fusion protein is produced in a eukaryotic expression system.

In an embodiment, the fusion protein produced in the eukaryotic expression system comprises glycosylation at a residue on the Fc portion corresponding to Asn297.

In an embodiment the composition or pharmaceutical composition comprising the antibody, or antigen-binding fragment thereof, described herein is substantially pure with regard to the antibody, or antigen-binding fragment thereof. A composition or pharmaceutical composition comprising the antibody, or antigen-binding fragment thereof, described herein is "substantially pure" with regard to the antibody or fragment when at least 60% to 75% of a sample of the composition or pharmaceutical composition exhibits a single species of the antibody, or antigen-binding fragment thereof. A substantially pure composition or pharmaceutical composition comprising the antibody, or antigen-binding fragment thereof, described herein can comprise, in the portion thereof which is the antibody, or antigen-binding fragment, 60%, 70%, 80% or 90% of the antibody, or antigen-binding fragment, of the single species, more usually about 95%, and preferably over 99%. Purity or homogeneity may be tested by a number of means well known in the art, such as polyacrylamide gel electrophoresis or HPLC.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention may be better understood from the Experimental Details, which follow.

EXPERIMENTAL DETAILS

Here are disclosed RBM-binding monoclonal antibodies (mAbs) that competitively inhibit the interaction of RBM of SARS-CoV-2 with human ACE2, and also specifically block the RBM-induced GM-CSF secretion in both human monocyte and murine macrophage cultures. The antibodies can be employed in a strategy to prevent a SARS-CoV-2-elicited "cytokine storm" and can also be used in assessment of innate immune-modulating properties of various SARS-CoV-2 vaccines.

Results

Figure 1A:
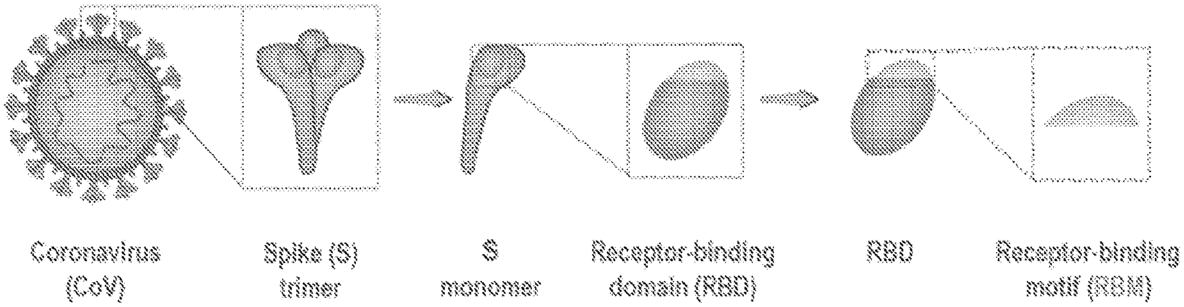
Figure 1C:
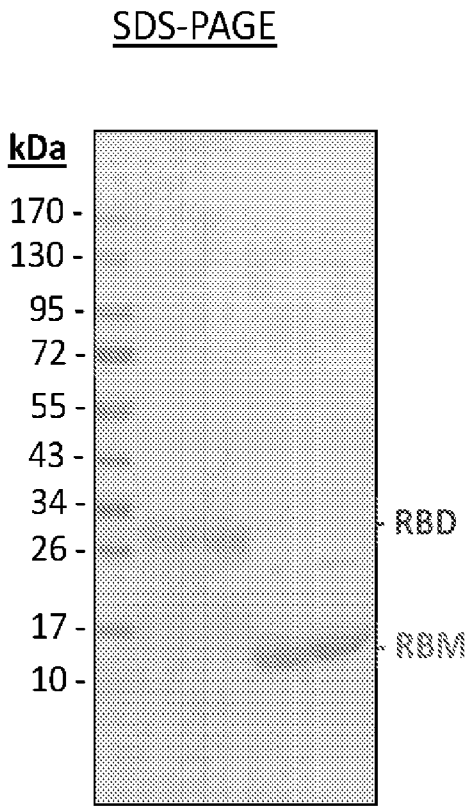

Generation of recombinant RBD and RBM protein fragments of SARS-CoV-2: To screen for monoclonal antibodies capable of binding the RBD or RBM region of SARS-CoV-2 spike protein (FIG. 1(A)), recombinant RBD and RBM were generated corresponding to residues 319-541 and residues 437-508 of SARS-CoV-2 spike (S) protein (FIG. 1(B)). These recombinant proteins were purified from insoluble inclusion bodies by differential centrifugation, urea solubilization, and histidine-tag affinity chromatography (FIG. 1(C)). Extensive washing of the immobilized recombinant RBD or RBM proteins with buffer containing 8.0 M urea effectively removed contaminating bacterial endotoxins. Subsequently, the purified RBD and RBM was dialyzed in a buffer supplemented with a reducing agent, Tris(2-carboxyethyl) phosphine (TCEP), to prevent excessive oxidation and cross-linking of the nine and two Cysteine (C) residues in RBD and RBM, respectively (FIG. 1(B)). Notably, several new strains of SARS-CoV-2 have emerged with multiple mutations, including the P.1 from Brazil and the B.1.351 from South Africa, which contain mutations in the ACE2 binding site (e.g., E484K, K417N/T, and N501Y) (FIG. 1D) that increased affinity for ACE2 [41] but reduced neutralization activities of some antibodies [42]. As shown in FIG. 1(E), amino acid sequence analysis revealed a high homology between a tyrosine (Y)-rich segment (YNYLYR) (SEQ ID NO:4) of SARS-CoV-2 RBM and the epitope sequence (NDALYEYLRQ) (SEQ ID NO:2) of several monoclonal antibodies (mAbs) that we recently generated against human tetranectin (TN) [23], suggesting a possibility that some TN-binding mAbs might cross-react with SARS-CoV-2.

Figures 2A, 2B:
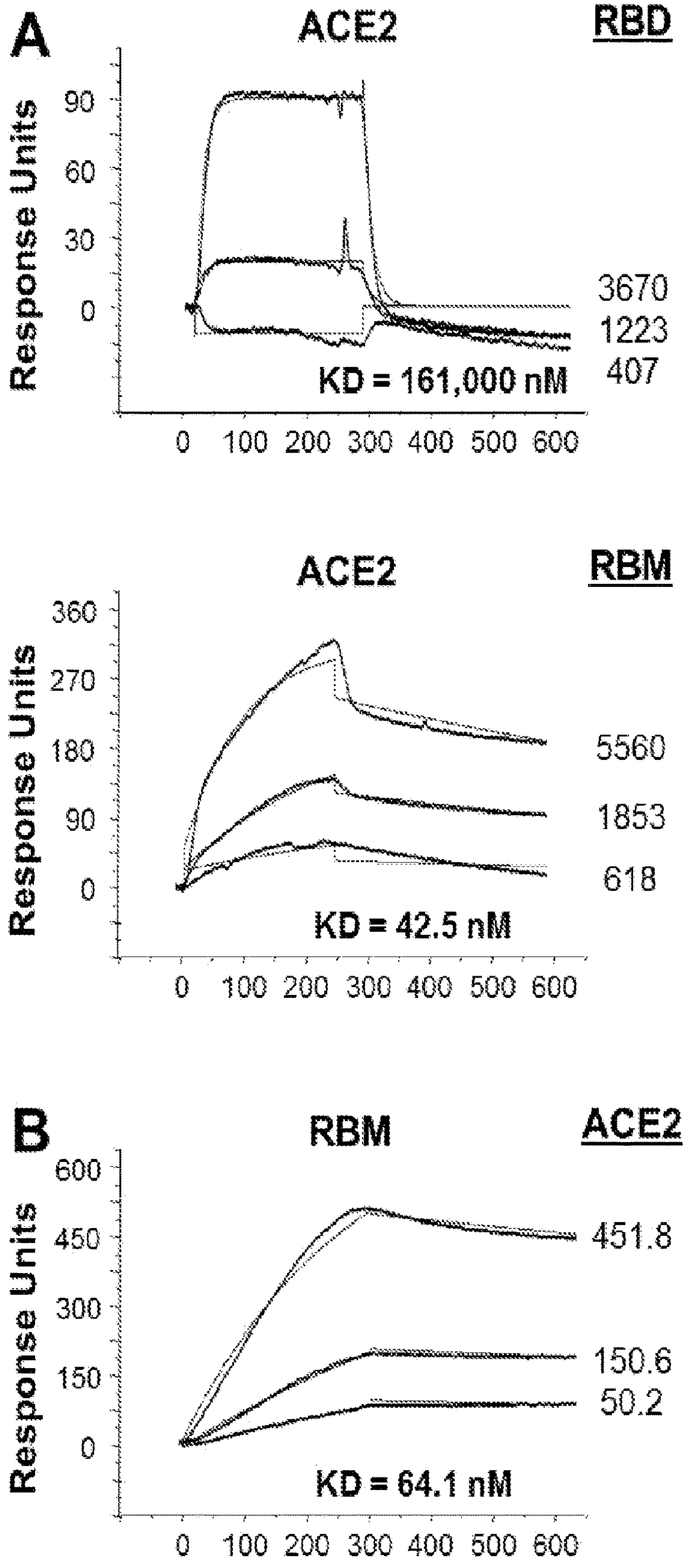
FIGS. 2(A)-2(D). Recombinant SARS-CoV-2 RBM binds to human ACE2 receptor and some TN-reactive mAbs. 2(A)

Recombinant RBM interacted with human ACE2 and some TN-binding mAbs: To evaluate the ACE2-binding properties of recombinant RBD or RBM, the extracellular domain of human ACE2 was immobilized to the NTA sensor chip, and recombinant RBD or RBM was applied as analytes at different concentrations to estimate the dissociation equilibrium constant ($K_D$) using the Open SPR technique. Surprisingly, the recombinant RBD exhibited an extremely low affinity to the extracellular domain of human ACE2 (FIG. 2(A), upper panel), with an estimated $K_D$ of 161,000 nM. It was postulated that the cysteine-rich RBD was not likely re-folded into a "correct" conformation suitable for RBM-ACE2 interaction, because the high probability of "incorrect" disulfide cross-linking was factorially proportional to its high number of Cysteine residues. In contrast, the $K_D$ for ACE2-RBM interaction ranged around 42.5-64.1 nM (FIG. 2(A), lower panel; FIG. 2(B)), regardless whether ACE2 or RBM was conjugated to the NTA sensor chip before respective application of RBM or ACE2 as analyte at different concentrations. Given the proximity between our estimated $K_D$ for RBM-ACE2 interaction and the previously reported $K_D$ (15-44.2 nM) for SARS-CoV-2 S protein-ACE2 interaction [12,18], it was concluded that the ACE2-binding property was well-preserved in our recombinant RBM. Therefore, a highly purified recombinant RBM was conjugated on an NTA sensor chip and used to screen for SARS-CoV-2 RBM-binding mAbs.

Figure 2C:
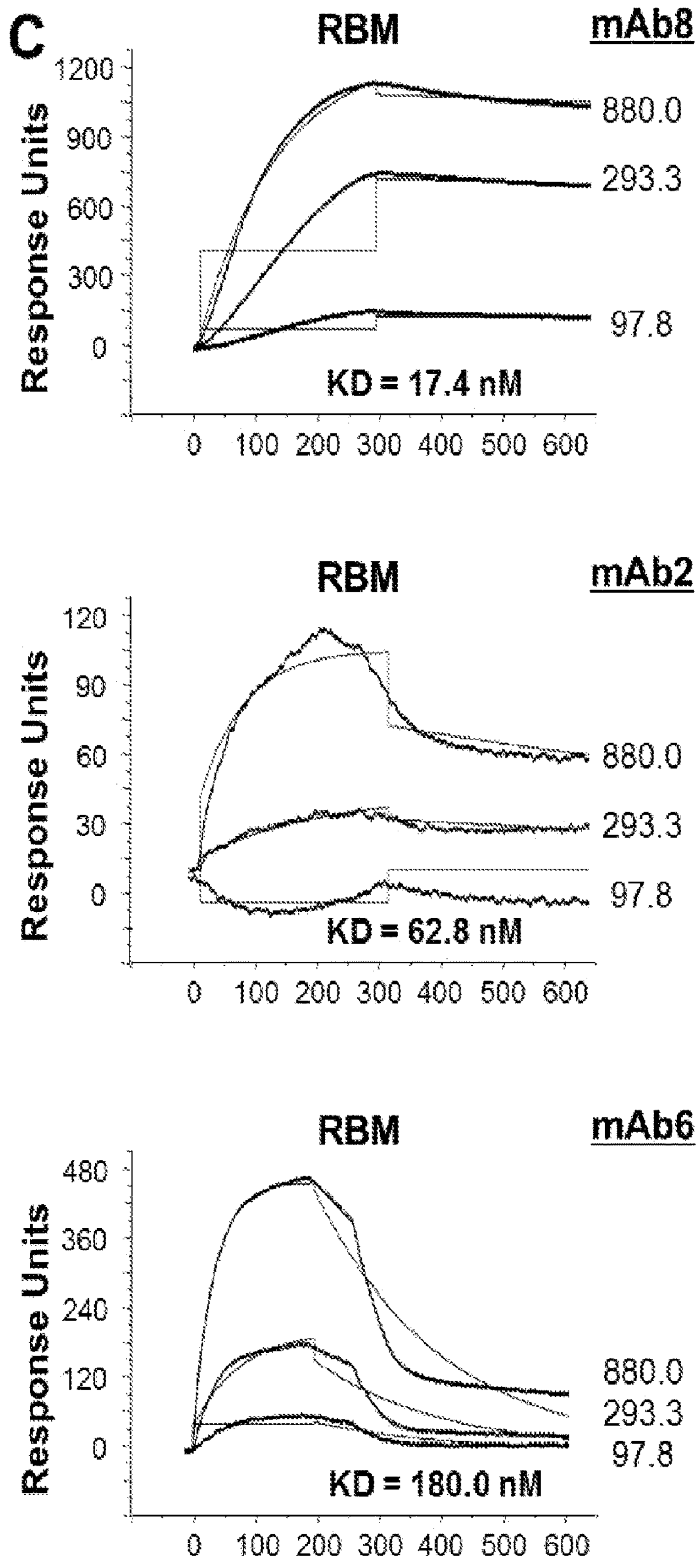
Figure 2D:
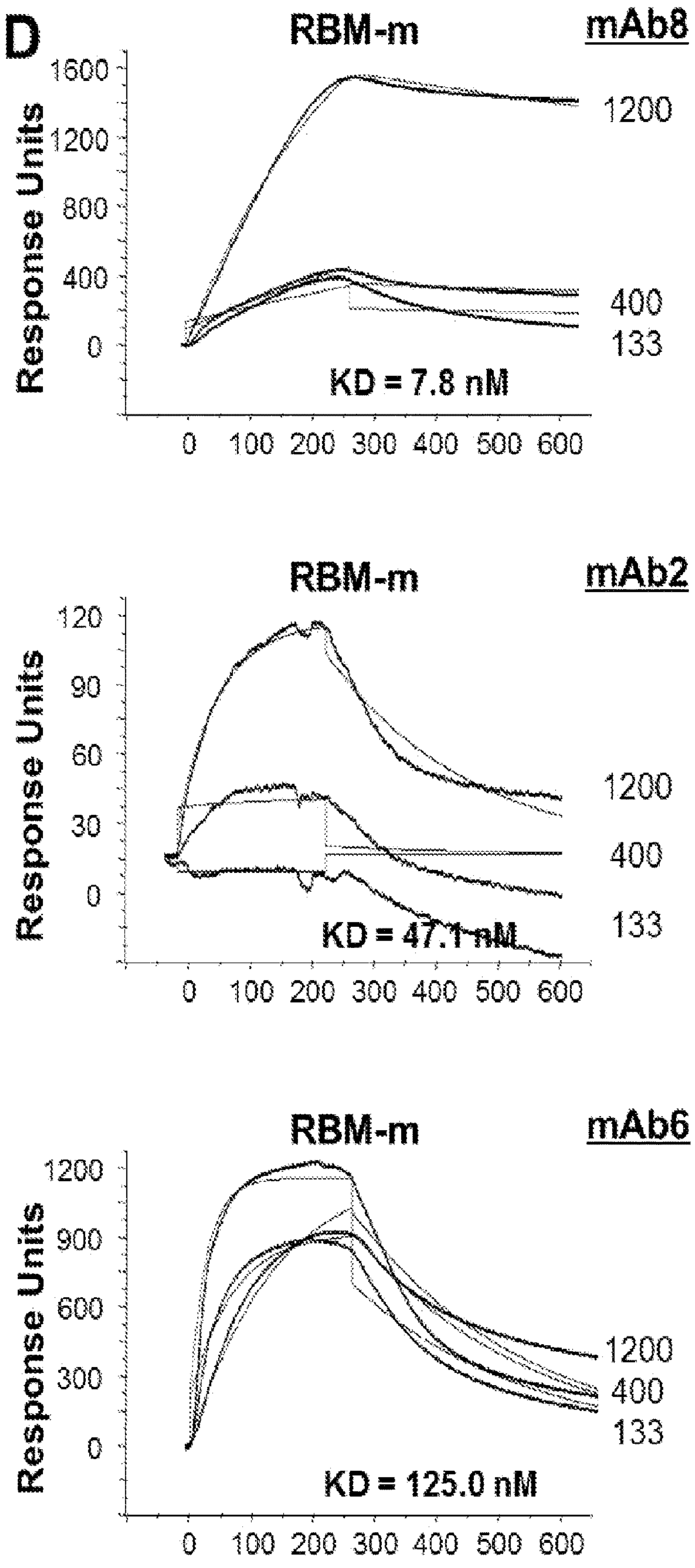

In agreement with a homology between SARS-CoV-2 RBM and epitope sequence of several TN-specific mAbs (FIG. 1(E)), it was found that 2 out of 3 mAbs capable of recognizing a homologous epitope sequence (NDALYEYLRQ) (SEQ ID NO:2) [23] exhibited a dose-dependent interaction with RBM (FIG. 2(C)), with an estimated $K_D$ of 17.4 and 62.8 nM, respectively. This estimated $K_D$ was comparable to that of other SARS-CoV-2 RBD-binding neutralizing antibodies ($K_D$=14-17 nM) recently isolated from COVID-19 patients [24, 25]. To confirm the binding properties of these mAbs to the RBM-m containing a point (E484K) mutation, recombinant RBM-m was immobilized on a sensor chip, and various mAbs were applied as analyte to assess the binding affinities. Consistently, mAb8 and mAb2 exhibited a higher affinity to RBM-m as compared to mAb6. Amino acid sequence analysis of the complementarity-determining regions (CDR) of these three different mAbs (mAb8, mAb2, and mAb6) revealed the presence of two distinct residues (Y and R) in the CDR1 and CDR2 of mAb6 (FIG. 11), which might underlie its relatively weaker affinity to RBM or RBM-m as compared with other two homologous mAbs (mAb8 and mAb2, FIG. 11).

RBM-binding mAbs competitively inhibited RBM-ACE2 interaction: It was then tested whether pre-treatment of RBM-conjugated sensor chip with RBM-binding mAb competitively inhibited subsequent RBM-ACE2 interactions. When conjugated to a sensor chip, the recombinant RBM exhibited a dose-dependent interaction with the extracellular domain of human ACE2 (FIG. 3(A)), as well as a RBM-binding mAb (mAb8) (FIG. 3(B)). However, after pre-treatment with mAb8, the maximal response unit was markedly reduced from ~500 (FIG. 3(A)) to 175 (FIG. 3(C)) when ACE2 was applied as analyte to the RBM-coated sensor chip at identical concentrations. Meanwhile, the estimated $K_D$ for RBM-ACE2 interaction was increased by an almost ten-fold from 13.3 nM (FIG. 3(A)) to 130.0 nM (FIG. 3(C)), suggesting that RBM-binding mAbs competitively RBM-ACE2 interactions.

RBM-binding mAbs specifically blocked the RBM-induced GM-CSF secretion in primary human peripheral blood mononuclear cells (huPBMCs): To examine the possible impact of RBM-binding mAbs on its immuno-stimulatory properties, human primary monocytes were stimulated with recombinant RBD or RBM in the absence or presence of RBM-binding mAbs (mAb8, mAb6 and mAb2, FIG. 5A, 5B) or irrelevant polyclonal antibodies (pAbs, FIG. 5B), and the levels of 42 different cytokines and chemokines were measured simultaneously by Antibody Arrays (FIG. 5C). In agreement with a previous report that SARS-CoV spike (S) protein stimulated human PBMCs to produce proinflammatory cytokines (e.g., IL-1β, IL-6, and TNF) [22], a marked elevation of these three cytokines was observed in the RBD- or RBM-stimulated human monocytes (FIG. 4(A), 4(B), 4(C)). In addition, both RBD and RBM also markedly stimulated the secretion of an anti-inflammatory cytokine (IL-10) and two chemokines (MIP-1δ and MCP-1) in parallel (FIG. 4(A), 4(B), 4(C)). Astonishingly, our highly purified RBM, but not RBD, also markedly induced the secretion of a myeloid growth factor, the granulocyte-macrophage colony-stimulating factor (GM-CSF) in human monocytes (FIG. 4(A), 4(B), 4(C)). However, the co-addition of two RBM-binding mAbs similarly and specifically blocked the RBM-induced secretion of GM-CSF (FIG. 4(A), 4(B), 4(C)) without affecting the RBM-induced release of other cytokines (e.g., IL-1β, IL-6, IL-10 and TNF) or chemokines (MIP-1δ and MCP-1).

RBM-binding mAbs also specifically blocked the RBM-induced GM-CSF secretion in murine macrophage-like RAW 264.7 cells: To further confirm the GM-CSF-inducing activities of SARS-CoV-2 RBM, murine macrophage-like RAW 264.7 cells were stimulated with highly purified RBM in the absence or presence of RBM-binding mAbs or irrelevant pAbs, and the extracellular levels of 62 different cytokines measured by Antibody Arrays. Compared with human monocytes, murine macrophages appeared to be less responsive to RBM stimulation and released relatively fewer cytokines after stimulation (FIG. 5(A)). However, SARS-CoV-2 RBM still markedly elevated the secretion of TNF and GM-CSF in murine macrophage cultures (FIG. 5(A)). Similarly, two different RBM-binding mAbs selectively blocked the RBM-induced GM-CSF secretion in macrophage cultures (FIG. 5(A), 5(B)) without affecting the RBM-induced TNF secretion (FIG. 5(A), 5(B)).

Although wild-type mice are less susceptible to SARS-CoV-2 infections, repetitive administration of recombinant RBM at extremely higher doses (600 μg/mouse) also led to a slight but significant increase of blood GM-CSF levels, which was similarly reduced by the co-administration of a RBM-neutralizing mAb8 (FIG. 5C). Our findings fully support the emerging notion that GM-CSF might be an important feature of SARS-CoV-2-induced cytokine storm in COVID-19 patients, and suggest an exciting possibility to attenuate the SARS-CoV-2-induced GM-CSF production and "cytokine storm" in clinical settings using vaccines capable of eliciting RBM-targeting antibodies.

RBM-binding mAbs also specifically blocked the RBM-m-induced GM-CSF secretion in human THP-1-derived macrophages: To further confirm the above findings, we repeated the experiments using recombinant RBM-m containing the E484K point mutation and macrophages derived from a human THP-1 monocyte cell lines. After pre-treatment of human THP-1 cells with for 2-3 days, the differentiated human macrophages were stimulated with highly purified RBD-m or RBM-m in the absence or presence of two different mAbs, and the extracellular levels of 42 different cytokines measured by Antibody Arrays. Although RBM-m similarly induced a marked release of IL-1β, IL-6, IL-10, MIP-1δ and GM-CSF in human macrophages (FIG. 6(A), 6(B)), mAb8 selectively and significantly blocked the RBM-m-induced GM-CSF secretion in macrophage cultures (FIG. 6(A), 6(B)) without affecting the RBM-induced secretion of other cytokines.

Discussion

In the present study, a highly purified recombinant RBM was generated corresponding to residues 437-508 of SARS-CoV-2, and its well-preserved ACE2-binding properties confirmed. Furthermore, two RBM-cross-reactive monoclonal antibodies that competitively inhibited RBM-ACE2 interaction and selectively inhibited the RBM-induced GM-CSF secretion in both human monocyte and murine macrophage cultures were identified.

This suggests that vaccines capable of eliciting RBM-targeting antibodies may similarly attenuate the SARS-CoV-2-induced GM-CSF production and "cytokine storm" in clinical settings. "Cytokine storm" refers a hyperactive inflammatory response manifested by the excessive infiltration, expansion and activation of myeloid cells (e.g., monocytes and macrophages) and consequent production of various cytokines and chemokines (e.g., GM-CSF, TNF, IL-1β, IL-6, and MCP-1). It has also been suggested as a "driver" of the disease progression particularly in a subset (~20%) of COVID-19 patients with more severe pneumonia that often escalates to respiratory failure and death 26-29.

Furthermore, GM-CSF might also be a mediator of the cytokine storm in COVID-19 and other inflammatory diseases [30,31]. First, GM-CSF was upregulated before TNF, IL-6, and MCP-1 in animal model of SARS-CoV infection [32], and its excessive production adversely contributed to the SARS-CoV-induced lung injury [32]. Second, consistent with the critical contribution of myeloid cells to cytokine storm [28], the percentages of GM-CSF-expressing leukocytes was significantly increased in a subset of patients with severe COVID-19 [33-34]. Thus, the excessive production of GM-CSF may adversely propagate a dysregulated cytokine storm in a subset of COVID-19 patients (FIG. 6(C)). On the one hand, GM-CSF can promote myelopoiesis by mobilizing progenitor myeloid cells to sites of SARS-CoV-2 infection and facilitating their proliferation and differentiation into various innate immune cells, such as monocytes, macrophages and dendritic cells [30]. On the other, GMCSF can also polarize mature myeloid cells into a pro-inflammatory phenotype and stimulate the production of various proinflammatory cytokines (e.g., TNF, IL-1β and IL-6) and chemokines (e.g., MCP-1) [30].

Currently, GM-CSF has attracted substantial interest as a therapeutic target for the clinical management of COVID-19 [31, 35]. For instance, several companies were planning for COVID-19 clinical trials using agents targeting GM-CSF (Clinical Trial Registry #: NCT04341116, NCT04351243, NCT04351152, NCT04376684) or GM-CSF receptor [31, 35, 36]. In a recent clinical study, repetitive intravenous infusion of an anti-human GM-CSF mAb (Lenzilumab, 600 mg, thrice) significantly improved blood oxygenation, and simultaneously reduced blood levels of two pro-inflammatory cytokines (e.g., IL-1a and IL-6) in 11 out of 12 patients with severe COVID-19 [37].

Materials and Methods

Materials: Murine macrophage-like RAW 264.7 cells were obtained from American Type Culture Collection (ATCC, Rockville, Md.). Dulbecco's modified Eagle medium (DMEM, 11995-065) and penicillin/streptomycin (Cat. 15140-122) were from Invitrogen/Life Technologies (Carlsbad, CA). Fetal bovine serum was from Crystalgen (FBS-500, Commack, NY) and heat-inactivated before use. The monoclonal antibodies against human tetranectin were generated in Balb/C and C57BL/6 mice at the GenScript (Piscataway, NJ, USA) as previously described [23]. Highly purified recombinant human ACE2 corresponding to the extracellular domain (Gln18-Ser740) was obtained from two different commercial sources, Biolegend (Cat. #7920008) and Raybiotech (Cat. #230-30165).

Cell culture: Human blood was purchased from the New York Blood Center (Long Island City, NY, USA), and human peripheral blood mononuclear cells (HuPBMCs) were isolated by density gradient centrifugation through Ficoll (Ficoll-Paque PLUS) as previously described [23]. Murine macrophages or human monocytes (HuBPMCs) were cultured in DMEM supplemented with 1% penicillin/streptomycin and 10% FBS or 10% human serum. When they reached 70-80% confluence, adherent cells were gently washed with, and immediately cultured in, OPTI-MEM I before stimulating with highly purified recombinant RBD or RBM in the absence or presence of anti-TN mAbs. The extracellular concentrations of various cytokines/chemokines were determined by Cytokine Antibody Arrays as previously described [39].

Preparation of recombinant RBD and RBM proteins: The cDNAs encoding for the ACE2 receptor binding domain (RBD, residue 319-541) or receptor binding motif (RBM, residue 437-508) of SARS-CoV-2 spike protein (S) were cloned into a pCAL-n vector, and the recombinant proteins with an N-terminal Histidine Tag (6×His) were expressed in *E. coli* BL21 (DE3) cells in the presence of 3.0 mM IPTG (isopropyl-1-thio-beta-D-galactopyranoside). Recombinant RBD and RBM proteins were isolated from the inclusion bodies by differential centrifugation, and further purified by urea (8.0 M Urea, 20 mM Tris-HCl, pH 8.9) solubilization and agarose bead-immobilized metal ($Ni^{2+}$) affinity chromatography. After extensive washing with buffer 1 (20 mM Tris-HCl, 10 mM imidazole, 0.5 M NaCl, 8.0 M Urea, pH 8.0) and buffer 2 (20% DPBS1×, 10% glycerol, 8.0 M Urea, pH 7.5), the recombinant histidine-tagged RBD or RBM proteins were eluted with buffer containing 0.5 M Imidazole, 10% Glycerol, 20% DPBS1×, 8.0 M Urea, pH 8.0. The recombinant proteins were then further purified by dialysis at 4° C. in buffer containing 20% DPBS1×, 10% Glycerol and 0.5 mM TCEP, pH8.0. Recombinant proteins were tested for LPS content by the chromogenic Limulus amebocyte lysate assay (Endochrome; Charles River), and the endotoxin content was less than 0.01 U per microgram of recombinant proteins.

Open Surface Plasmon Resonance (SPR): The Nicoya Lifesciences gold-nanoparticle-based Open Surface Plasmon Resonance (OpenSPR) technology was used to estimate the binding kinetics and affinity of ACE2 or monoclonal antibodies to SARS-CoV-2 RBD or RBM following the manufacturer's instructions. For instance, highly purified recombinant RBD or RBM was immobilized on the NTA sensor chip (Cat. #SEN-Au-100-10-NTA), and ACE2 or mAb was applied at different concentrations. The response units were recorded over time, and the binding affinity was estimated as the equilibrium dissociation constant $K_D$ using the Trace Drawer Kinetic Data Analysis v.1.6.1. (Nicoya Lifesciences) as previously described [23]. To determine the possible competition with the human ACE2, SARS-CoV-2 RBM was immobilized to NTA sensor chips via histidine tag for a final RU around 500. A RBM-binding mAb was injected onto the chip until binding steady-state was reached, and ACE2 was re-injected as analyte at identical concentrations. The competition capacity of RBM-binding mAb was determined by the level of reduction in response units of ACE2 with and without prior mAb incubation. Results presented are representatives of two independent experiments.

Cytokine Antibody Array: Human Cytokine Antibody C3 Arrays (Cat. No. AAH-CYT-3-4), which detect 42 cytokines on one membrane, were used to determine cytokine concentrations in human monocyte-conditioned culture medium as previously described [23]. Murine Cytokine Antibody Arrays (Cat. No. M0308003, RayBiotech Inc.), which simultaneously detect 62 cytokines on one membrane, were used to measure relative cytokine concentrations in macrophage-conditioned culture medium as described previously [23,40].

Statistical analysis: All data were assessed for normality by the Shapiro-Wilk test before conducting statistical tests among multiple groups by one-way analyses of variance (ANOVA) followed by the Fisher Least Significant Difference (LSD) test. A P value <0.05 was considered statistically significant.

Sequences of antibodies (framework regions in sequence underlined, signal sequences italicized):

Clone 27B12 (mAb8) heavy chain DNA Sequence(SEQ ID NO: 5).

Clone 27B12: Heavy Chain DNA Sequence (408 bp)
Signal sequence-FR1-CDR1-FR2-CDR2-FR3-CDR3-FR4

SEQ ID NO 5

*ATGAACTTCGGGCTCAGATTGATTTTCCTTGTCCTTGTTTTAAAAGGTGTCCTGTGT*GACGTGAAGC

TCGTGGAGTCTGGGGGAGGCTTAGTGAAGCTTGGAGGGTCCCTGAAACTCTCCTGTGCAGCCTCTGG

ATTCACTTTCAGTACCGATTACATGTCTTGGGTTCGCCAGAGTCCAGAGAAGAGGCTGGAGTTGGTC

GCAGCCATTAATAGTAATGGTGGTACCACCTACTATCCAGACACTGTGAAGGGCCGATTCATCATCT

CCAGAGACAATGCCAAGAACACCCTGTACCTGCAAATGAGCAGTCTGAGGTCTGAGGACACAGCCTT

-continued

GTATTACTGTGCAAGACAGGTTAAGAATGGTCTGGACTACTGGGGTCAAGGAACCTCAGTCACCGTC

TCCTCA

Clone 27B1 (mAb8) heavy chain amino acid Sequence(SEQ ID NO: 6).
Clone 27B12: Heavy Chain Amino Acid Sequence (136 aa)
Signal peptide-FR1-CDR1-FR2-CDR2-FR3-CDR3-FR4

SEQ ID NO 6

*MNFGLRLIFLVLVLKGVLC*DVKLVESGGGLVKLGGSLKLSCAASGFTFSTDYMSWVRQSPEKRLELVA

AINSNGGTTYYPDTVKGRFIISRDNAKNTLYLQMSSLRSEDTALYYCARQVKNGLDYWGQGTSVTVSS

Clone 27B12 (mAb8) light chain DNA sequence(SEQ ID NO: 7).
Clone 27B12: Light Chain DNA Sequence (381 bp)
Signal sequence-FR1-CDR1-FR2-CDR2-FR3-CDR3-FR4

SEQ ID NO 7

*ATGATGTCCTCTGCTCAGTTCCTTGGTCTCCTGTTGCTCTGTTTTCAAGGTACCAGATGT*GATATCC

AGATGACACAGACTACATCCTCCCTGTCTGCCTCTCTGGGAGACAGAGTCACCATCAGTTGCAGGGC

AAGTCAGGACATTAGCAATTATTTAAACTGGTATCAGCAGAAACCAGATGGAACTGTCAAACTCCTG

ATCTACAAAACTTCTAGATTACACTCAGGAGTCCCATCAAGGTTCAGAGGCAGTGGGTCTGGAACAG

ATTATTCTCTCACCATTAGCAACCTGGAGGAAGAAGATGTTGCCACTTACTTTTGCCAACAGGGTAA

TACGCTTCCTCCGACGTTCGGTGGAGGCACCAAGCTGGAAATCAAA

Clone 27B 12 (mAb8) light chain amino acid sequence(SEQ ID NO: 8).
Clone 27B12: Light Chain Amino Acid Sequence (127 aa)
Signal peptide-FR1-CDR1-FR2-CDR2-FR3-CDR3-FR4

SEQ ID NO 8

*MMSSAQFLGLLLLCFQGTRC*DIQMTQTTSSLSASLGDRVTISCRASQDISNYLNWYQQKPDGTVKLL

IYKTSRLHSGVPSRFRGSGSGTDYSLTISNLEEEDVATYFCQQGNTLPPTFGGGTKLEIK

Clone 25B2 (mAb6) heavy chain DNA Sequence(SEQ ID NO: 9).
Clone 25B2: Heavy Chain DNA Sequence (408 bp)
Signal sequence-FR1-CDR1-FR2-CDR2-FR3-CDR3-FR4

SEQ ID NO 9

*ATGAACTTCGGGCTCAGATTGATTTTCCTTGTCCTTGTTTTAAAAGGTGTCCTGTGT*GACGTGAACC

TCGTGGAGTCGGGGGGAGGCTTAGTGAAGCTTGGAGGGTCCCTGAAACTCTCCTGTGCAGACTCTGG

ATTCACTTTCAGTAGCTATTACATGTCTTGGGTTCGCCAGACTCCAGAGAAGAGGCTGGAGTTGGTC

GCAGCCATTAATAGTAATGGTGGTAGGACCTACTATCCAGACACTGTGAAGGGCCGATTCACCATCT

CCAGAGACAATGCCAAGAACACCCTGTACCTGCAAATGAGCAGTCTGAAGTCTGAGGACACAGCCTT

GTATTACTGTGCAAGACAGGGTAAGAATGGTTTGGACTACTGGGGTCAAGGAACCTCAGTCACCGTC

TCCTCA

Clone 25B2 (mAb6) heavy chain amino acid Sequence(SEQ ID NO: 10).
Clone 25B2: Heavy Chain Amino Acid Sequence (136 aa)
Signal peptide-FR1-CDR1-FR2-CDR2-FR3-CDR3-FR4

SEQ ID NO 10

*MNFGLRLIFLVLVLKGVLC*DVNLVESGGGLVKLGGSLKLSCADSGFTFSSYYMSWVRQTPEKRLELVA

AINSNGGRTYYPDTVKGRFTISRDNAKNTLYLQMSSLKSEDTALYYCARQGKNGLDYWGQGTSVTVSS

Clone 25B2 (mAb6) light chain DNA sequence(SEQ ID NO: 11)

Clone 25B2: Light Chain DNA Sequence (378 bp)
Signal sequence-FR1-CDR1-FR2-CDR2-FR3-CDR3-FR4

SEQ ID NO 11

*ATGTCCTCTGCTCAGTTCCTTGGTCTCCTGTTGCTCTGTTTTCAAGGTACCAGATGT*GATATCCAGA

TGACACAGACCACATCCTCCCTGTCTGCCTCTCTGGGAGACAGAGTCACCATCAGTTGCAGGGCAAG

TCAGGACATTAGTAATCATTTAAACTGGTATCAGCAGAAACCAGATGGAACTATTAAACTCCTGATC

TACTATACATCAAGATTACACTCAGGAGTCCCATCAAGGTTCAGTGGCAGTGGGTCTGGAACTGATT

TTTCTCTCAGCATTAGCAACCTGGAGCAAGAGGATATTGCCACTTACTTTTGCCAACAGGGTAAAAC

GCTTCCTCCGACGTTCGGTGGAGGCACCAAACTGGAAATCAAA

Clone 25B2 (mAb6) light chain amino acid sequence(SEQ ID NO: 12).

-continued

Clone 25B2: Light Chain Amino Acid Sequence (126 aa)
Signal peptide-FR1-CDR1-FR2-CDR2-FR3-CDR3-FR4

SEQ ID NO 12

*MSSAQFLGLLLLCFQGTRC*DIQMTQTTSSLSASLGDRVTISCRASQDISNHLNWYQQKPDGTIKLLIY

YTSRLHSGVPSRFSGSGSGTDFSLSISNLEQEDIATYFCQQGKTLPPTFGGGTKLEIK

Clone 23F6 (mAb5) heavy chain DNA Sequence(SEQ ID NO: 13).
Clone 23F6: Heavy Chain DNA Sequence (408 bp)
Signal sequence-FR1-CDR1-FR2-CDR2-FR3-CDR3-FR4

SEQ ID NO 13

*ATGAACTTCGGGCTCAGATTGATTTTCCTTGTCCTTGTTTTAAAAGGTGTCCTGTGT*GACGTGAAGC

TCGTGGAGTCTGGGGGTGGCTTAGTGAAACTTGGAGGGTCCCTGAAACTCTCCTGTGCAGCCTCTGG

ATTCACTTTCAGTAGCTCTTACATGTCTTGGGTTCGCCAGACTCCAGAGAAGAGGCTGGAGTTGGTC

GCAGCCATTAATAATAATGGTGGTACCACCTACTATCCAGACACTGTGAAGGGCCGATTCACTATCT

CCAGAGACAATGCCAAGAACACCCTGTACCTGCAAATGAGCAGTCTGAAGTCTGAGGACACAGCCTT

GTATTATTGTACAAGACAGGGTAAGAATGGTTTGGACTACTGGGGTCAAGGAACCTCAGTCACCGTC

TCCTCA

Clone 23F6 (mAb5) heavy chain amino acid Sequence(SEQ ID NO: 14).
Clone 23F6: Heavy Chain Amino Acid Sequence (136 aa)
Signal peptide-FR1-CDR1-FR2-CDR2-FR3-CDR3-FR4

SEQ ID NO 14

*MNFGLRLIFLVLVLKGVLC*DVKLVESGGGLVKLGGSLKLSCAASGFTFSSSYMSWVRQTPEKRLELVA

AINNNGGTTYYPDTVKGRFTISRDNAKNTLYLQMSSLKSEDTALYYCTRQGKNGLDYWGQGTSVTVSS

Clone 23F6 (mAb5) light chain DNA sequence(SEQ ID NO: 15).
Clone 23F6: Light Chain DNA Sequence (378 bp)
Signal sequence-FR1-CDR1-FR2-CDR2-FR3-CDR3-FR4

SEQ ID NO 15

*ATGTCCTCTGCTCAGTTCCTTGGTCTCCTGTTGCTCTGTTTTCAAGGTACCAGATGT*GATATCCAGA

TGACACAGACTACATCCTCCCTGTCTGCCTCTCTGGGAGACAGAGTCACCATCAGTTGCAGGGCCAG

TCAGGACATTGGCAATCTTTTAAACTGGTATCAGCAGAAACCAGATGGAACTGTTAAACTCCTGATC

TCCTACACATCAAGATTACACTCAGGAGTCCCATCAAGGTTCAGTGGCAGTGGGTCTGGAACAGATT

ATTCTCTCACCATTACCAACCTGGAACAAGAAGATATTGCCACTTACTTTTGCCAACAGGCTAATAC

GCTTCCTCCGACGTTCGGTGGAGGCTCCAAGCTGGAAATCAAA

Clone 23F6 (mAb5) light chain amino acid sequence(SEQ ID NO: 16).
Clone 23F6: Light Chain Amino Acid Sequence (126 aa)
Signal peptide-FR1-CDR1-FR2-CDR2-FR3-CDR3-FR4

SEQ ID NO 16

*MSSAQFLGLLLLCFQGTRC*DIQMTQTTSSLSASLGDRVTISCRASQDIGNLLNWYQQKPDGTVKLLI

SYTSRLHSGVPSRFSGSGSGTDYSLTITNLEQEDIATYFCQQANTLPPTFGGGSKLEIK

Clone 18B1 (mAb2) heavy chain DNA Sequence(SEQ ID NO: 17).
Clone 18B1: Heavy Chain DNA Sequence (408 bp)
Signal sequence-FR1-CDR1-FR2-CDR2-FR3-CDR3-FR4

SEQ ID NO 17

*ATGAACTTCGGGCTCAGATTGATTTTCCTTGTCCTTGTTTTAAAAGGTGTCCTGTGT*GACGTGAAGC

TCGTGGAGTCTGGGGGAGGCTTAGTGAACCTTGGAGGGTCCCTGAAACTCTCCTGTGCAGCCTCTGG

ATTCACTTTCAGTAGCGATTACATGTCTTGGGTTCGCCAGATTCCAGAGAAGAGGCTGGAGTTGGTC

GCAGCCATTAATAGTAATGGTGGTACCACCTACTATCCAGACACTGTGAAGGGCCGATTCACCATCT

CCAGAGACAATGCCAAGAACACCCTGTACCTGCAAATGAGCAGTCTGAAGTCTGAGGACACAGCCTT

GTATTACTGTGCAAGACAGGGTAAGAATGGTATGGACTACTGGGGTCAAGGAACCTCAGTCACCGTC

TCCTCA

Clone 18B12 (mAb2) heavy chain amino acid Sequence(SEQ ID NO: 18).
Clone 18B1: Heavy Chain Amino Acid Sequence (136 aa)
Signal peptide-FR1-CDR1-FR2-CDR2-FR3-CDR3-FR4

SEQ ID NO 18

*MNFGLRLIFLVLVLKGVLC*DVKLVESGGGLVNLGGSLKLSCAASGFTFSSDYMSWVRQIPEKRLELVA

-continued

AINSNGGTTYYPDTVKGRFTISRDNAKNTLYLQMSSLKSEDTALYYCARQGKNGMDYWGQGTSVTVSS

Clone 18B12 (mAb2) light chain DNA sequence(SEQ ID NO: 19).
Clone 18B1: Light Chain DNA Sequence (378 bp)
Signal sequence-FR1-CDR1-FR2-CDR2-FR3-CDR3-FR4

SEQ ID NO 19

*ATGTCCTCTGCTCAGTTCCTTGGTCTCCTGTTGCTCTGTTTTCAAGGTACCAGATGT*GATATCCAGAT

GACACAGACTACATCCTCCCTGTCTGCCTCTCTGGGAGACAGAGTCACCATCAGTTGCAGGGCAAGTC

AGGACATTAGCAATCATTTAAACTGGTATCAGCAGAGACCAGATGGAACTGTTAAACTCCTGATCTAC

TACACATCAAGATTACACTCAGGAGTCCCATCAAGGTTCAGTGGCAGTGGGTCTGGAACAGATTATTC

TTTCACCATTACCAACCTTGATCAAGAAGATATTGCCACTTACTTTTGCCAACAGGGTAAGACGCTTC

CTCCGACGTTCGGTGGAGGCACCAAGCTGGAAATCAAA

Clone 18B1 (mAb2) light chain amino acid sequence(SEQ ID NO: 20).
Clone 18B1: Light Chain Amino Acid Sequence (126 aa)
Signal peptide-FR1-CDR1-FR2-CDR2-FR3-CDR3-FR4

SEQ ID NO 20

*MSSAQFLGLLLLCFQGTRC*DIQMTQTTSSLSASLGDRVTISCRASQDISNHLNWYQQRPDGTVKLLIY

YTSRLHSGVPSRFSGSGSGTDYSFTITNLDQEDIATYFCQQGKTLPPTFGGGTKLEIK

REFERENCES

1. Hwang, W. C. et al. Structural basis of neutralization by a human anti-severe acute respiratory syndrome spike protein antibody, 80R. *J. Biol. Chem.* 281, 34610-34616 (2006).
2. Zhou, P. et al. A pneumonia outbreak associated with a new coronavirus of probable bat origin. *Nature.* 579, 270-273 (2020).
3. Zhou, D. et al. Structural basis for the neutralization of SARS-CoV-2 by an antibody from a convalescent patient. *Nat. Struct. Mol. Biol.* 10-0480 (2020).
4. Zost, S. J. et al. Potently neutralizing and protective human antibodies against SARS-CoV-2. *Nature.* 10-2548 (2020).
5. Barnes, C. O. et al. Structures of Human Antibodies Bound to SARS-CoV-2 Spike Reveal Common Epitopes and Recurrent Features of Antibodies. *Cell.* 10 (2020).
6. Ju, B. et al. Human neutralizing antibodies elicited by SARS-CoV-2 infection. *Nature.* 10-2380 (2020).
7. Lan, J. et al. Structure of the SARS-CoV-2 spike receptor-binding domain bound to the ACE2 receptor. *Nature.* 581, 215-220 (2020).
8. Hoffmann, M. et al. SARS-CoV-2 Cell Entry Depends on ACE2 and TMPRSS2 and Is Blocked by a Clinically Proven Protease Inhibitor. *Cell.* 181, 271-280 (2020).
9. Walls, A. C. et al. Structure, Function, and Antigenicity of the SARS-CoV-2 Spike Glycoprotein. *Cell.* 181, 281-292 (2020).
10. Sternberg, A. & Naujokat, C. Structural features of coronavirus SARS-CoV-2 spike protein: Targets for vaccination. *Life Sci.* 257:118056. doi: 10.1016/j.lfs.2020.118056., 118056 (2020).
11. Yan, R. et al. Structural basis for the recognition of SARS-CoV-2 by full-length human ACE2. *Science.* 367, 1444-1448 (2020).
12. Shang, J. et al. Structural basis of receptor recognition by SARS-CoV-2. *Nature.* 581, 221-224 (2020).
13. McCallum, M., Walls, A. C., Bowen, J. E., Corti, D., & Veesler, D. Structure-guided covalent stabilization of coronavirus spike glycoprotein trimers in the closed conformation. *Nat. Struct. Mol. Biol.* 10-0483 (2020).
14. Wang, Q. et al. Structural and Functional Basis of SARS-CoV-2 Entry by Using Human ACE2. *Cell.* 181, 894-904 (2020).
15. Amanat, F. & Krammer, F. SARS-CoV-2 Vaccines: Status Report. *Immunity.* 52, 583-589 (2020).
16. Pinto, D. et al. Cross-neutralization of SARS-CoV-2 by a human monoclonal SARS-CoV antibody. *Nature.* 583, 290-295 (2020).
17. Walls, A. C. et al. Unexpected Receptor Functional Mimicry Elucidates Activation of Coronavirus Fusion. *Cell.* 176, 1026-1039 (2019).
18. Wrapp, D. et al. Cryo-EM structure of the 2019-nCoV spike in the prefusion conformation. *Science.* 367, 1260-1263 (2020).
19. Wang, Q. et al. Immunodominant SARS Coronavirus Epitopes in Humans Elicited both Enhancing and Neutralizing Effects on Infection in Non-human Primates. *ACS Infect. Dis.* 2, 361-376 (2016).
20. Obitsu, S. et al. Potential enhancement of osteoclastogenesis by severe acute respiratory syndrome coronavirus 3a/X1 protein. *Arch. Virol.* 154, 1457-1464 (2009).
21. Zhang, D. et al. COVID-19 infection induces readily detectable morphological and inflammation-related phenotypic changes in peripheral blood monocytes, the severity of which correlate with patient outcome. *medRxiv*2020 (2020).
22. Dosch, S. F., Mahajan, S. D., & Collins, A. R. SARS coronavirus spike protein-induced innate immune response occurs via activation of the NF-kappaB pathway in human monocyte macrophages in vitro. *Virus Res.* 142, 19-27 (2009).
23. Chen, W. et al. Identification of tetranectin-targeting monoclonal antibodies to treat potentially lethal sepsis. *Sci. Transl. Med.* 12, 12-539 (2020).
24. Rogers, T. F. et al. Isolation of potent SARS-CoV-2 neutralizing antibodies and protection from disease in a small animal model. *Science*.eabc7520 (2020).
25. Yuan, M. et al. Structural basis of a shared antibody response to SARS-CoV-2. *Science*.eabd2321 (2020).
26. Mehta, P. et al. COVID-19: consider cytokine storm syndromes and immunosuppression. *Lancet.* 395, 1033-1034 (2020).
27. Wang, J., Jiang, M., Chen, X., & Montaner, L. J. Cytokine storm and leukocyte changes in mild versus severe SARS-CoV-2 infection: Review of 3939 COVID-19 patients in China and emerging pathogenesis and therapy concepts. *J Leukoc. Biol.* 108, 17-41 (2020).

28. Jafarzadeh, A., Chauhan, P., Saha, B., Jafarzadeh, S., & Nemati, M. Contribution of monocytes and macrophages to the local tissue inflammation and cytokine storm in COVID-19: Lessons from SARS and MERS, and potential therapeutic interventions. *Life Sci.* 257:118102. doi: 10.1016/j.lfs.2020.118102., 118102 (2020).
29. Wu, Z. & McGoogan, J. M. Characteristics of and Important Lessons From the Coronavirus Disease 2019 (COVID-19) Outbreak in China: Summary of a Report of 314 Cases From the Chinese Center for Disease Control and Prevention. *JAMA.* 10 (2020).
30. Hamilton, J. A. GM-CSF in inflammation. *J Exp. Med.* 217, e20190945 (2020).
31. Hamilton, J. A., Cook, A. D., & Tak, P. P. Anti-colony-stimulating factor therapies for inflammatory and autoimmune diseases. *Nat. Rev. Drug Discov.* 16, 53-70 (2016).
32. Channappanavar, R. et al. Dysregulated Type I Interferon and Inflammatory Monocyte-Macrophage Responses Cause Lethal Pneumonia in SARS-CoV-Infected Mice. *Cell Host. Microbe.* 19, 181-193 (2016).
33. Huang, C. et al. Clinical features of patients infected with 2019 novel coronavirus in Wuhan, China. *Lancet.* 395, 497-506 (2020).
34. Zhou, Y. et al. Pathogenic T-cells and inflammatory monocytes incite inflammatory storms in severe COVID-19 patients. *National Science Review* 7[6], 998-1002. 2020.
35. Lang, F. M., Lee, K. M., Teijaro, J. R., Becher, B., & Hamilton, J. A. GM-CSF-based treatments in COVID-19: reconciling opposing therapeutic approaches. *Nat. Rev. Immunol.* 20, 507-514 (2020).
36. Mehta, P. et al. Therapeutic blockade of granulocyte macrophage colony-stimulating factor in COVID-19-associated hyperinflammation: challenges and opportunities. *Lancet Respir. Med.* 8, 822-830 (2020).
37. Temesgen, Z. et al. First Clinical Use of Lenzilumab to Neutralize GM-CSF in Patients with Severe COVID-19 Pneumonia. *medRxiv.* 2020 (2020).
38. Dagotto, G., Yu, J., & Barouch, D. H. Approaches and Challenges in SARS-CoV-2 Vaccine Development. *Cell Host. Microbe.* 10 (2020).
39. Chen, W. et al. Enhanced Macrophage Pannexin 1 Expression and Hemichannel Activation Exacerbates Lethal Experimental Sepsis. *Sci. Rep.* 9, 160-37232 (2019).
40. Li, W. et al. Connexin 43 Hemichannel as a Novel Mediator of Sterile and Infectious Inflammatory Diseases. *Sci. Rep.* 8, 166-18452 (2018).
41. Dejnirattisai W, Zhou D, Supasa P, Liu C, Mentzer A J, Ginn H M, Zhao Y, Duyvesteyn H M E, Tuekprakhon A, Nutalai R, Wang B, LÃ³pez-Camacho C, Slon-Campos J, Walter T S, Skelly D, Costa Clemens S A, Naveca F G, Nascimento V, Nascimento F, Fernandes da C C, Resende P C, Pauvolid-Correa A, Siqueira M M, Dold C, Levin R, Dong T, Pollard A J, Knight J C, Crook D, Lambe T, Clutterbuck E, Bibi S, Flaxman A, Bittaye M, Belij-Rammerstorfer S, Gilbert S C, Carroll M W, Klenerman P, Barnes E, Dunachie S J, Paterson N G, Williams M A, Hall D R, Hulswit R J G, Bowden T A, Fry E E, Mongkolsapaya J, Ren J, Stuart D I, Screaton G R (2021) Antibody evasion by the P. 1 strain of SARS-CoV-2. Cell 10.
42. Jangra S, Ye C, Rathnasinghe R, Stadlbauer D, Krammer F, Simon V, Martinez-Sobrido L, GarcÃ-a-Sastre A, Schotsaert M (2021) SARS-CoV-2 spike E484K mutation reduces antibody neutralisation. Lancet Microbe-9.

What is claimed is:

1. A method of:

(i) inhibiting binding of severe acute respiratory syndrome coronavirus 2 (SARS-COV-2) to an ACE2 receptor;

(ii) inhibiting a SARS-COV-2 infection of, and/or SARS-COV-2-induced GM-CSF production in, a cell comprising an ACE2 receptor; or (iii) treating a subject for a SARS-COV-2 infection;

comprising administering an amount of an antibody, or a SARS-COV-2 ACE2 Receptor Binding Motif (RBM)-binding fragment thereof, comprising a) a heavy chain variable region comprising:

(SEQ ID NO: 21) TDYMS, (SEQ ID NO: 22) AINSNGGTTYYPDTVKG, and (SEQ ID NO: 23) QVKNGLDY;

and a light chain variable region comprising:

(SEQ ID NO: 24) RASQDISNYLN, (SEQ ID NO: 25) KTSRLHS, and (SEQ ID NO: 26) QQGNTLPPT;

or b) a heavy chain variable region comprising:

(SEQ ID NO: 27) SYYMS, (SEQ ID NO: 28) AINSNGGRTYYPDTVKG, and (SEQ ID NO: 29) QGKNGLDY;

-continued and a light chain variable region comprising:

(SEQ ID NO: 30) RASQDISNHLN, (SEQ ID NO: 31) YTSRLHS, and (SEQ ID NO: 32) QQGKTLPPT;

or c) a heavy chain variable region comprising:

(SEQ ID NO: 33) SSYMS, (SEQ ID NO: 34) AINNNGGTTYYPDTVKG, and (SEQ ID NO: 35) QGKNGLDY;

and a light chain variable region comprising:

(SEQ ID NO: 36) RASQDIGNLLN, (SEQ ID NO: 37) YTSRLHS, and (SEQ ID NO: 38) QQANTLPPT;

or d) a heavy chain variable region comprising:

(SEQ ID NO: 39) SDYMS, (SEQ ID NO: 40) AINSNGGTTYYPDTVKG, and (SEQ ID NO: 41) QGKNGMDY;

and a light chain variable region comprising:

(SEQ ID NO: 42) RASQDISNHLN, (SEQ ID NO: 43) YTSRLHS, and

-continued (SEQ ID NO: 44)
QQGKTLPPT.

2. The method of claim 1, wherein the antibody, or antigen-binding fragment thereof, binds to a sequence NDALYEYLRQ (SEQ ID NO:2) of a human tetranectin or a sequence in RBM domain of SARS-COV-2 (residues (SEQ ID NO:4 and/or residues 437-508 of SEQ ID NO: 3).

3. The method of claim 1, wherein the antibody, or antigen-binding fragment thereof, comprises a heavy chain variable region comprising:

(SEQ ID NO: 21)
TDYMS, (SEQ ID NO: 22)
AINSNGGTTYYPDTVKG, and (SEQ ID NO: 23)
QVKNGLDY;

and a light chain variable region comprising:

(SEQ ID NO: 24)
RASQDISNYLN, (SEQ ID NO: 25)
KTSRLHS, and (SEQ ID NO: 26)
QQGNTLPPT.

4. The method of claim 1, wherein the antibody, or antigen-binding fragment thereof, comprises a heavy chain variable region comprising:

(SEQ ID NO: 27)
SYYMS, (SEQ ID NO: 28)
AINSNGGRTYYPDTVKG, and (SEQ ID NO: 29)
QGKNGLDY;

and a light chain variable region comprising:

(SEQ ID NO: 30)
RASQDISNHLN, (SEQ ID NO: 31)
YTSRLHS, and (SEQ ID NO: 32)
QQGKTLPPT.

5. The method of claim 1, wherein the antibody, or antigen-binding fragment thereof, comprises a heavy chain variable region comprising:

(SEQ ID NO: 33)
SSYMS, (SEQ ID NO: 34)
AINNNGGTTYYPDTVKG, and (SEQ ID NO: 35)
QGKNGLDY;

and a light chain variable region comprising:

(SEQ ID NO: 36)
RASQDIGNLLN,

-continued (SEQ ID NO: 37)
YTSRLHS, and (SEQ ID NO: 38)
QQANTLPPT.

6. The method of claim 1, wherein the antibody, or antigen-binding fragment thereof, comprises a heavy chain variable region comprising:

(SEQ ID NO: 39)
SDYMS, (SEQ ID NO: 40)
AINSNGGTTYYPDTVKG, and (SEQ ID NO: 41)
QGKNGMDY;

and a light chain variable region comprising:

(SEQ ID NO: 42)
RASQDISNHLN, (SEQ ID NO: 43)
YTSRLHS, and (SEQ ID NO: 44)
QQGKTLPPT.

7. The method of claim 1, wherein the antibody, or antigen-binding fragment thereof, comprises framework regions of the light chain and/or the heavy chain which are human framework regions, or have 85% or more identity thereto.

8. The method of claim 7, wherein framework regions of the light chain and/or the heavy chain are human framework regions.

9. The method of claim 1, wherein the antibody or antigen-binding fragment thereof binds to a sequence NDALYEYLRQ (SEQ ID NO:2) of a human tetranectin or a sequence in RBM domain of SARS-COV-2 (SEQ ID NO:4 and/or residues 437-508 of SEQ ID NO: 3) with an affinity of 3.0 nM $K_D$ or stronger.

10. The method of claim 1, wherein the antibody or antigen-binding fragment thereof binds to a sequence NDALYEYLRQ (SEQ ID NO:2) of a human tetranectin or a sequence in RBM domain of SARS-COV-2 (SEQ ID NO:4 and/or residues 437-508 of SEQ ID NO: 3) with an affinity of 2.0 nM $K_D$ or stronger.

11. The method of claim 1, wherein the antibody or antigen-binding fragment thereof has a human sequence Fc region.

12. The method of claim 1, wherein the antibody or fragment thereof is chimeric or humanized.

13. The method of claim 1, wherein the antibody or fragment thereof is selected from the group consisting of a monoclonal antibody, an scFv, an Fab fragment, an Fab' fragment, an F (ab)' fragment and a bispecific antibody.

14. The method of claim 1, wherein the antibody is a humanized antibody and is an IgG1 (2) or an IgG2 (2).

15. The method of claim 1, which inhibits interaction between an ACE2 Receptor Binding Motif (RBM) of a spike protein of a SARS-COV-2 and an ACE2 Receptor.

16. The method of claim 1, wherein the antibody or antigen-binding fragment thereof binds to an ACE2 Receptor Binding Motif (RBM) of a spike protein of a SARS-CoV-2 with an affinity of 2.0 nM $K_D$ or stronger.

17. The method of claim 1, wherein the antibody or antigen-binding fragment thereof binds to an ACE2 Receptor Binding Motif (RBM) of a spike protein of a SARS-CoV-2 with an affinity of 10.0 nM $K_D$ or stronger.

18. The method of claim 1, wherein the antibody or antigen-binding fragment thereof binds to an ACE2 Receptor Binding Motif (RBM) of a spike protein of a SARS-CoV-2 with an affinity of 20.0 nM $K_D$ or stronger.

* * * * *